“”

US007074771B2

(12) United States Patent
Jessell et al.

(10) Patent No.: US 7,074,771 B2
(45) Date of Patent: Jul. 11, 2006

(54) GENE ENCODING MNR2 AND USES THEREOF

(75) Inventors: Thomas M. Jessell, New York, NY (US); Yasuto Tanabe, Kyoto (JP); Christopher William, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 498 days.

(21) Appl. No.: 10/095,932

(22) Filed: Mar. 11, 2002

(65) Prior Publication Data
US 2002/0197678 A1 Dec. 26, 2002

Related U.S. Application Data

(62) Division of application No. 09/162,524, filed on Sep. 29, 1998, now Pat. No. 6,387,656.

(51) Int. Cl.
*A61K 31/70* (2006.01)
*A61K 39/00* (2006.01)
*C12N 5/02* (2006.01)
*C12N 15/63* (2006.01)

(52) U.S. Cl. ............... 514/44; 536/23.5; 424/198.1; 435/375; 435/455

(58) Field of Classification Search ............... 435/455, 435/325, 69.1, 377; 514/44, 2
See application file for complete search history.

(56) References Cited

U.S. PATENT DOCUMENTS

| 6,387,656 B1 | 5/2002 | Jessell et al. | |
|---|---|---|---|
| 2003/0104374 A1* | 6/2003 | Jessell et al. ............ | 435/6 |

FOREIGN PATENT DOCUMENTS

WO    WO 0018884    4/2000

OTHER PUBLICATIONS

Roelink et al (Cell 81: 445-455), 1995).*
Bowie et al (Science 247: 1306-1310, 1990).*
Rudinger (In Peptide Hormones J.A. Parsons, Ed. University Park Press, Baltimore, 1976, pp. 1, 6, and 7).*
Ngo et al (In The Protein Folding Problem and Tertiary Structure Prediction, K. Merz Jr. and S. Legrand, Eds. Birkhauser, Boston, 1994, pp. 433 and 492-495. ).*
Vollmer et al (J. Neurochem. 71(1): 1-19, Jul. 1998).*
Hagger (J. Anim. Sci. 70: 2045-2052, 1992).*
Anderson, D.J. et al. (1997) The Determination of the Neuronal Phenotype. *In Molecular and Cellular Approaches to Neural Development*, Eds. Cowan, W.M., Jessell, T.M., and Zipursky, S.L. Oxford University Press, New York, Oxford, pp. 26-63.

Arber et al. (1999) Requirement for the Homeobox Gene Hb9 in the Consolidation of Motor Neuron Identity, *Neuron* 23:659-674.
Bang, A.G. et al. (1996) Regulation of Vertebrate Neural Cell Fate by Transcription Factors, *Curr. Opin. Neurobiol.* 6:25-32.
Basler, K. et al. (1993) Control of Cell Pattern in the Neural Tube: Regulation of Cell Differentiation by Dorsalin-1, a Novel TGF Beta Family Member, *Cell* 73:687-702.
Begley, C.G. et al. (1992) Molecular Characterization of nscl, a Gene Encoding a Helix-loop-helix Protein Expressed in the Developing Nervous System, *Proc. Natl. Acad. Sci. USA* 89:38-42.
Branch. *Trends in Biochemical Sciences* 23: 45-50; 1998.
Burke, A.C. et al. (1996) Virally Mediated Misexpression of Hoxc-6 in the Cervical Mesoderm Results in Spinal Nerve Truncations, *Dev. Biol.* 178:192-197.
Chen, R. et al. (1997) Dachshund and Eyes Absent Proteins Form a Complex and Function Synergistically to Induce Ectopic Eye Development in Drosophila, *Cell* 91:893-903.
Chiang, C. et al. (1996) Cyclopia and Defective Axial Patterning in Mice Lacking Sonic Hedgehog Gene Function, *Nature* 383:407-413.
Crook *In Basic Principles of Antisense Therapeutics*, (1998) Springer-Verlag, Eds, New York, pp. 1 and 4.
Database Tumor Gene Index. Accession No. A1560820. NCI-CGAP. National Cancer Institute, Cancer Genome Anatomy Project (CGAP), Tumor Gene Index. Jun. 1998.

(Continued)

*Primary Examiner*—Richard Schnizer
(74) *Attorney, Agent, or Firm*—John P. White, Esq.; Cooper & Dunham LLP

(57) ABSTRACT

This invention provides an isolated nucleic acid molecule encoding a motor neuron restricted pattern, MNR2, protein. This invention provides an isolated nucleic acid molecule of at least 15 contiguous nucleotides capable of specifically hybridizing with a unique sequence included within the sequence of the nucleic acid molecule encoding a MNR2 protein. This invention provides a purified MNR2 protein, a polyclonal and monoclonal antibody directed to an epitope of an MNR2 protein. This invention provides a method of inducing differentiation somatic motor neurons which comprises expressing MNR2 protein in any neural progenitor cells. This invention provides a transgenic animal which expresses an MNR2 protein. This invention provides a pharmaceutical composition comprising a MNR2 protein and pharmaceutically acceptable carrier. This invention provides methods of treating subjects afflicted with an abnormality associated with a lack of normally functioning motor neurons, neurodegenerative disease, an acute nervous system injury and a neuromuscular disease which comprises contacting the subject with a pharmaceutical composition comprising a MNR2 protein and pharmaceutically acceptable carrier. This invention provides a functionally equivalent analog of MNR2 that induces or prevents MNR2 differentiation of neural progenitor cells.

4 Claims, 15 Drawing Sheets

OTHER PUBLICATIONS

Deguchi et al. (1991) Nucleotide Sequence of a Novel Diverged Human Homeobox Gene Encodes a DNA Binding Protein, *Nucleic Acids Research* 19:3742.

Ding, Q. et al. (1998) Diminished Sonic Hedgehog Signaling and Lack of Floor Plate Differentiation in Gli2 Mutant Mice, *Development* 125:2533-2543.

Ericson, J. et al. (1992) Early Stages of Motor Neuron Differentiation Revealed by Expression of Homeobox Gene Islet-1, *Science* 256:1555-60.

Ericson, J. et al. (1996) Two Critical Periods of Sonic Hedgehog Signaling Required for the Specification of Motor Neuron Identity, *Cell* 87:661-673.

Ericson, J. et al. (1997) Pax6 Controls Progenitor Cell Identity and Neuronal Fate in Response to Graded Shh Signaling, *Cell* 90:169-180.

Fedtsova, N. et al. (1997) Inhibitory Effects of Ventral Signals on the Development of Brn-3.0-expressing Neurons in the Dorsal Spinal Cord, *Dev. Biol.* 190:18-31.

Halder, G. et al. (1995) Induction of Ectopic Eyes by Targeted Expression of the Eyeless Gene in Drosophila, *Science* 267:1788-1792.

Harrison, K.A. et al. (1994) a Novel Human Homeobox Gene Distantly Related to Proboscipedia Is Expressed in Lymphoid and Pancreatic Tissues, *The Journal of Biological Chemistry* 269:19968-19975.

Hynes, M. et al. (1997) Control of Cell Pattern in the Neural Tube by the Zinc Finger Transcription Factor and Oncogene Gli-1, *Neuron* 19:15-26.

Ingham, P.W. (1995) Signaling by Hedgehog Family Proteins in Drosophila and Vertebrate Development, *Curr. Opin. Genet. Dev.* 5:492-498.

Jurata, L.W. et al. (1998) the Nuclear Lim Domain Interactor Nli Mediates Homo-and Heterodimerization of Lim Domain Transcription Factors, *J. Biol. Chem.* 273:3152-3157.

Langman, J. et al. (1966) Behavior of Neuroepithelial Cells During Closure of the Neural Tube, *J. Comp. Neurol.* 127:399-411.

Leber, S.M. and Sanes, J.R. (1995) Migratory Paths of Neurons and Glia in the Embryonic Chick Spinal Cord, *J. Neurosci.* 15:1236-1248.

Lee, J. et al. (1997) Gli1 Is a Target of Sonic Hedgehog That Induces Ventral Neural Tube Development, *Development* 124:2537-2552.

Liem, K.F. et al. (1997) A Role for the Roof Plate and its Resident TGFbeta-related Proteins in Neuronal Patterning in the Dorsal Spinal Cord, *Cell* 91:127-138.

Lo, L. et al. (1998) MASH1 Activates Expression of the Paired Homeodomain Transcription Factor Phox2a, and Couples Pan-neuronal and Subtype-specific Components of Autonomic Neuronal Identity, *Development* 125:609-620.

Lumsden, A. et al. (1996) Patterning the Vertebrate Neuraxis, *Science* 274:1109-1115.

Marti, E. et al. (1995) Requirement of 19k Form of Sonic Hedgehog for Induction of Distinct Ventral Cell Types, *Nature* 375:322-325.

Matise M.P. et al. (1998) Gli2 Is Required for Induction of Floor Plate and Adjacent Cells, but Not Most Ventral Neurons in the Mouse Central Nervous System, *Development* 125:2759-2770.

Osumi, N. et al. (1997) Pax-6 Is Involved in Specification of the Hindbrain Motor Neuron Subtype, *Development* 124:2961-2972.

Pabst, O. et al. (1998) Nkx2-9 Is a Novel Homeobox Transcription Factor Which Demarcates Ventral Domains in the Developing Mouse CNS, *Mech. Dev.* 73:85-93.

Pattyn, A. et al. (1997) Expression and Interactions of the Two Closely Related Homeobox Genes Phox2a and Phox2b During Neurogenesis, *Development* 124: 4065-4075.

Pfaff, S. L. et al. (1996) Requirement for LIM Homeobox Gene Isl1 in Motor Neuron Generation Reveals a Motor Neuron-dependent Step in Interneuron Differentiation, *Cell* 84:309-320.

Pfaff, S. et al. (1998) Neuronal Diversification: Development of Motor Neuron Subtypes, *Curr. Opin. Neurobiol.* 8:27-36.

Pharmacia Biotech catalogue (1995) p. 277.

Pharmacia Biotech catalogue (1995) pp. 104-111.

Pignoni, F. et al. (1997) The Eye-Specification Proteins So and Eya Form a Complex and Regulate Multiple Steps in Drosophila Eye Development, *Cell* 91:881-891.

Riddle, R.D. et al. (1995) Induction Of the LIM Homeobox Gene Lmx1 by WNT7a Establishes Dorsoventral Pattern in the Vertebrate Limb, *Cell* 83:631-640.

Roelink, H. et al. (1995) Floor Plate and Motor Neuron Induction by Different Concentrations of the Amino-Terminal Cleavage Product of Sonic Hedgehog Autoproteolysis, *Cell* 81:445-455.

Roztocil, T. et al. (1997) NeuroM, a Neural Helix-loop-helix Transcription Factor, Defines a New Transition Stage in Neurogenesis, *Development* 124:3263-3272.

Ruiz i Altaba et al. (1993) Ectopic Neural Expression of a Floor Plate Marker in Frog Embryos Injected with the Midline Transcription Factor Pintallavis, *Proc. Natl. Acad. Sci. USA* 90:8268-8272.

Ruiz i Altaba et al. (1995) Restrictions to Floor Plate Induction by Hedgehog and Winged-helix Genes in the Neural Tube of Frog Embryos, *Mol. Cell Neurosci.* 6:106-121.

Saha, M.S. et al. (1997) Dorsal-Ventral Patterning During Neural Induction in Xenopus: Assessment of Spinal Cord Regionalization with xHB9, a Marker for the Motor Neuron Region, *Dev. Biol.* 187:209-223.

Sasaki, H. et al. (1994) HNF-3 Beta as a Regulator of Floor Plate Development, *Cell* 76:103-115.

Schaeren-Wiemers, N. et al. (1993) A Single Protocol to Detect Transcripts of Various Types and Expression Levels in Neural Tissue and Cultured Cells: in Situ Hybridization Using Digoxigenin-labeled cRNA Probes, *Histochemistry* 100:431-440.

Tanabe, Y. et al. (1995) Induction of Motor Neurons by Sonic Hedgehog Is Independent of Floor Plate Differentiation, *Curr. Biol.* 5:651-658.

Tanabe, Y. et al. (1996) Diversity and Pattern in the Developing Spinal Cord, *Science* 274:1115-1123.

Tanabe, Y. et al. (1998) Specification of Motor Neuron Identity by the MNR2 Homeodomain Protein, *Cell* 95:67-80.

Tanaka, H. et al. (1984) Developmental Changes in Unique Cell Surface Antigens of Chick Embryo Spinal Motor Neurons and Ganglion Cells, *Dev. Biol.* 106:26-37.

Thaler et al. (1999) Active Suppression of Interneuron Programs with Developing Motor Neurons Revealed by Analysis of Homeodomain Factor HB9, *Neuron* 23:675-687.

Tsuchida, T. (1994) Topographic Organization of Embryonic Motor Neurons Defined by Expression of LIM Homeobox Genes, *Cell* 79:957-70.

Varela-Echavarría, A. et al. (1996) Differential Expression of LIM Homeobox Genes among Motor Neuron Subpopulations in the Developing Chick Brain Stem. *Mol. Cell. Neurosci.* 8:242-257.

Weintraub, H. (1993) The MyoD Family and Myogenesis: Redundancy, Networks, and Thresholds, *Cell* 75:1241-1244.

Westendorf, J.M. et al. (1994) Cloning of cDNAs for M-Phase Phosphoproteins Recognized by the MPM2 Monoclonal Antibody and Determination of the Phosphorylated Epitope, *Proc. Natl. Acad. Sci. USA* 91:714-718; and.

Yamada, T. et al. (1993) Control of Cell Pattern in the Neural Tube: Motor Neuron Induction of Diffusible Factors From Notochord and Floor Plate, *Cell* 73:673-686.

Supplementary Partial European Search Report issued by the European Patent Office on Nov. 10, 2004 in connection with European Patent Application No. 99949964.3, filed Apr. 27, 2001, European Publication No. 111761, published Jul. 25, 2001, on behalf of The Trustees of Columbia University in the City of New York.

* cited by examiner

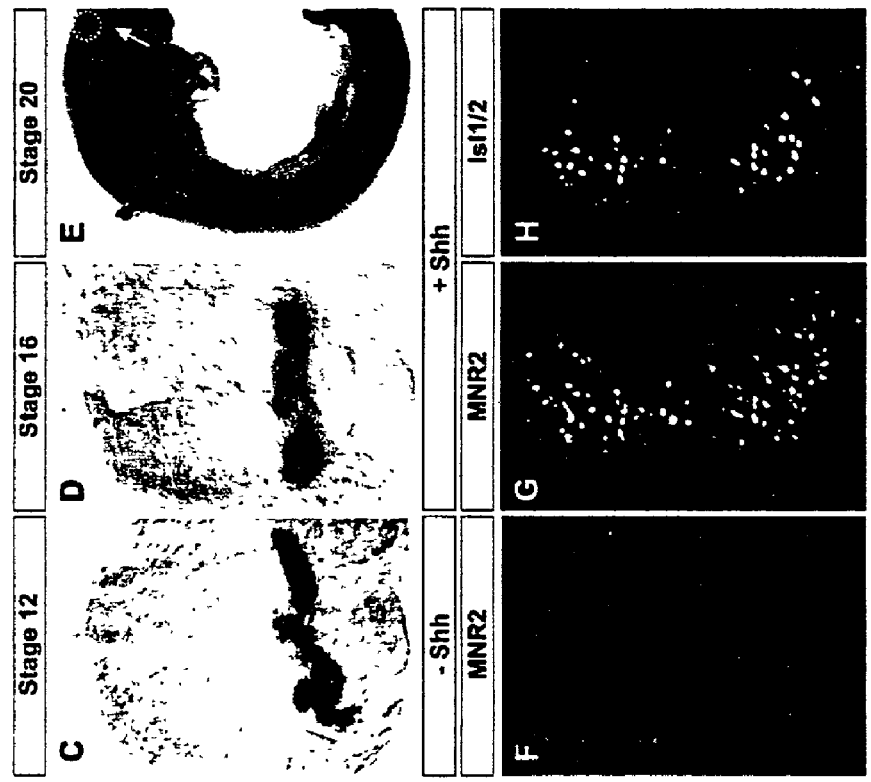
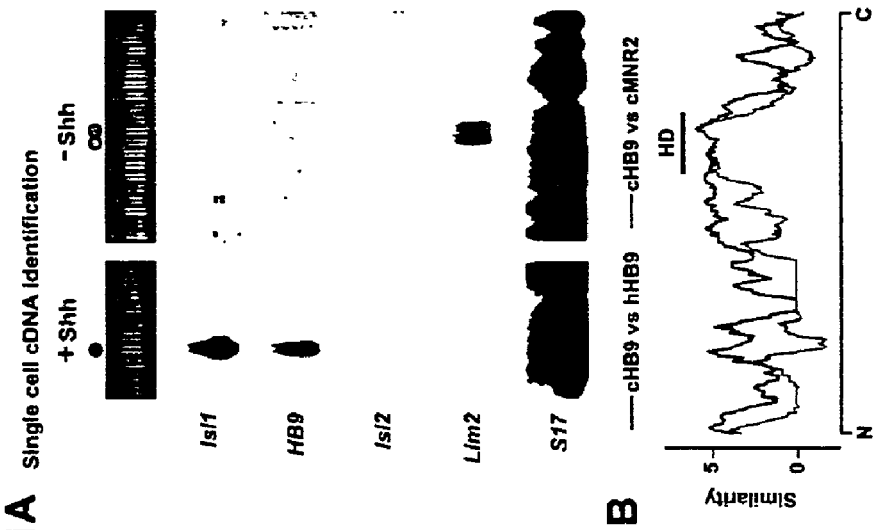
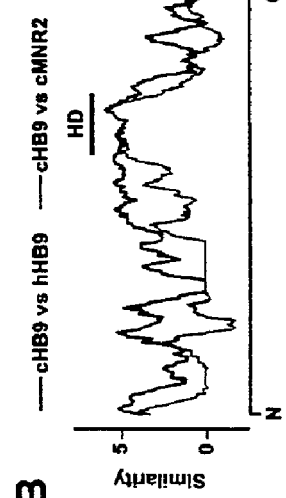

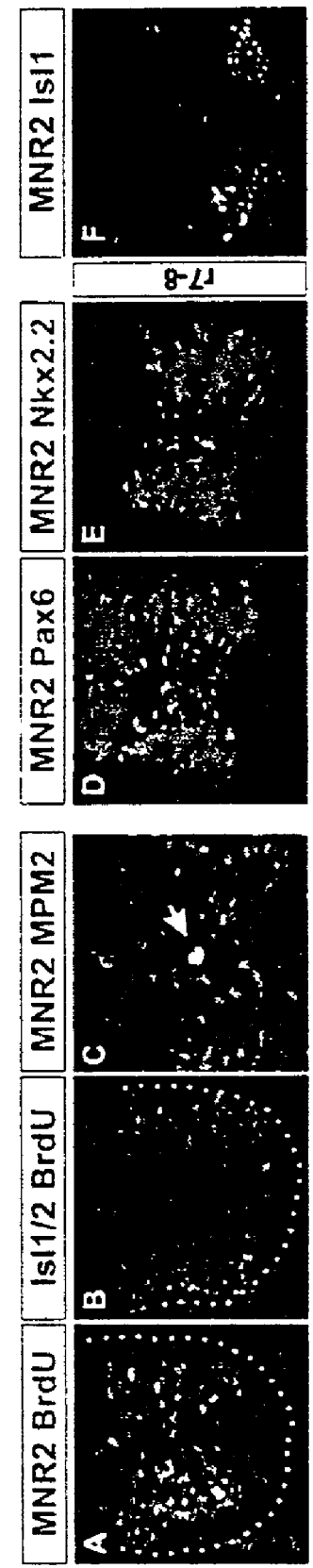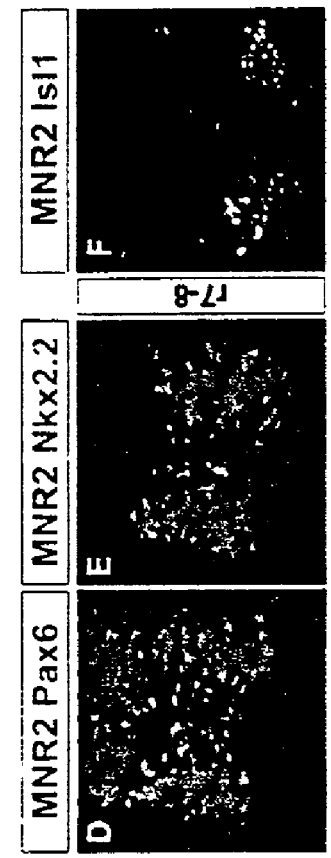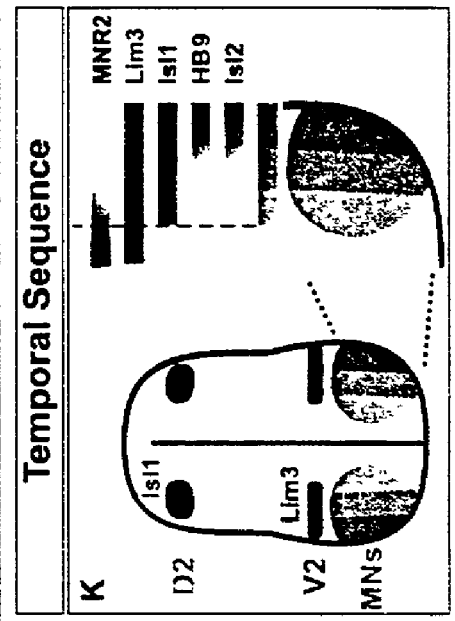
FIG. 2A FIG. 2B FIG. 2C FIG. 2D FIG. 2E FIG. 2F
FIG. 2G FIG. 2H FIG. 2I FIG. 2J FIG. 2K

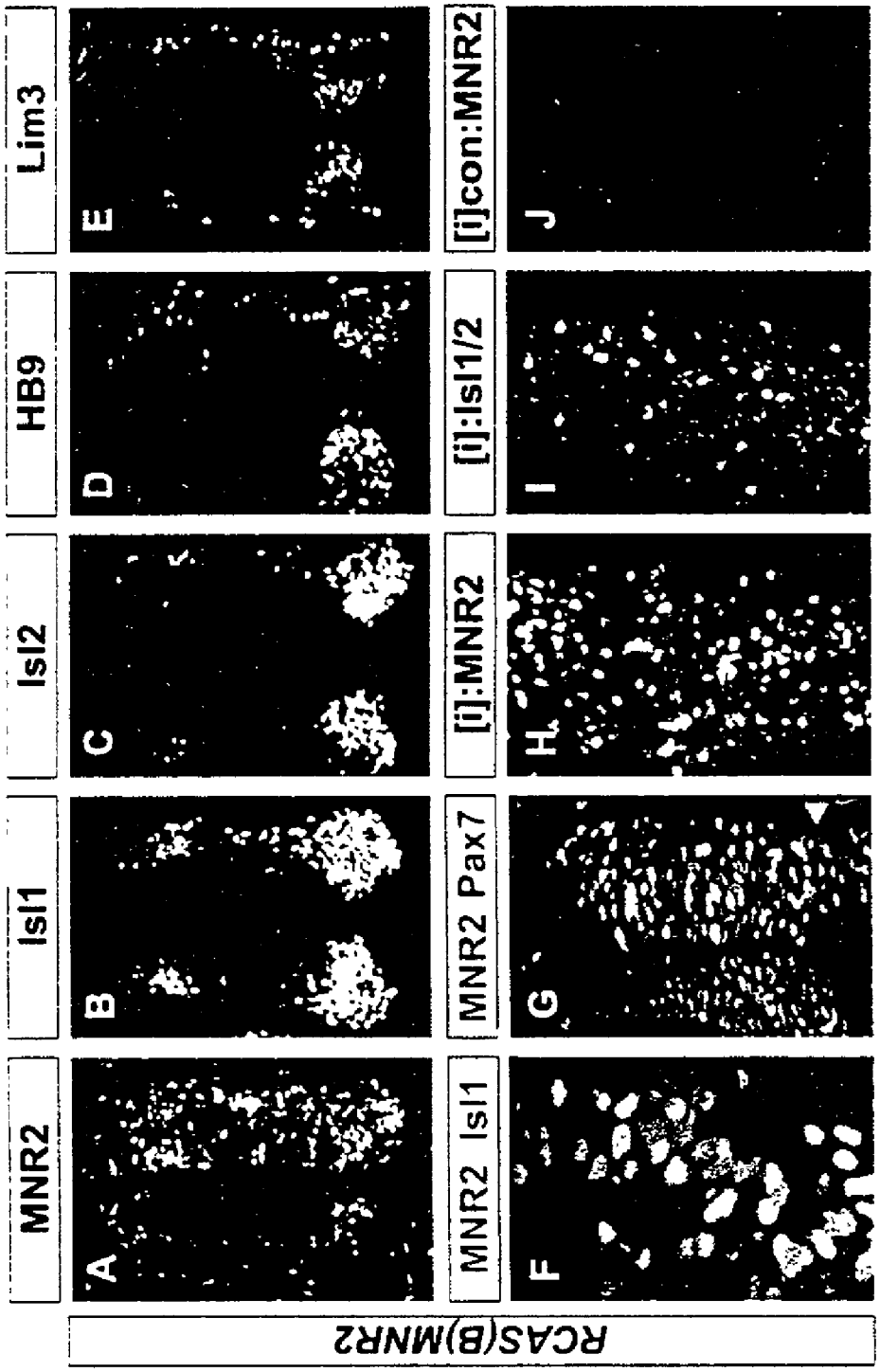

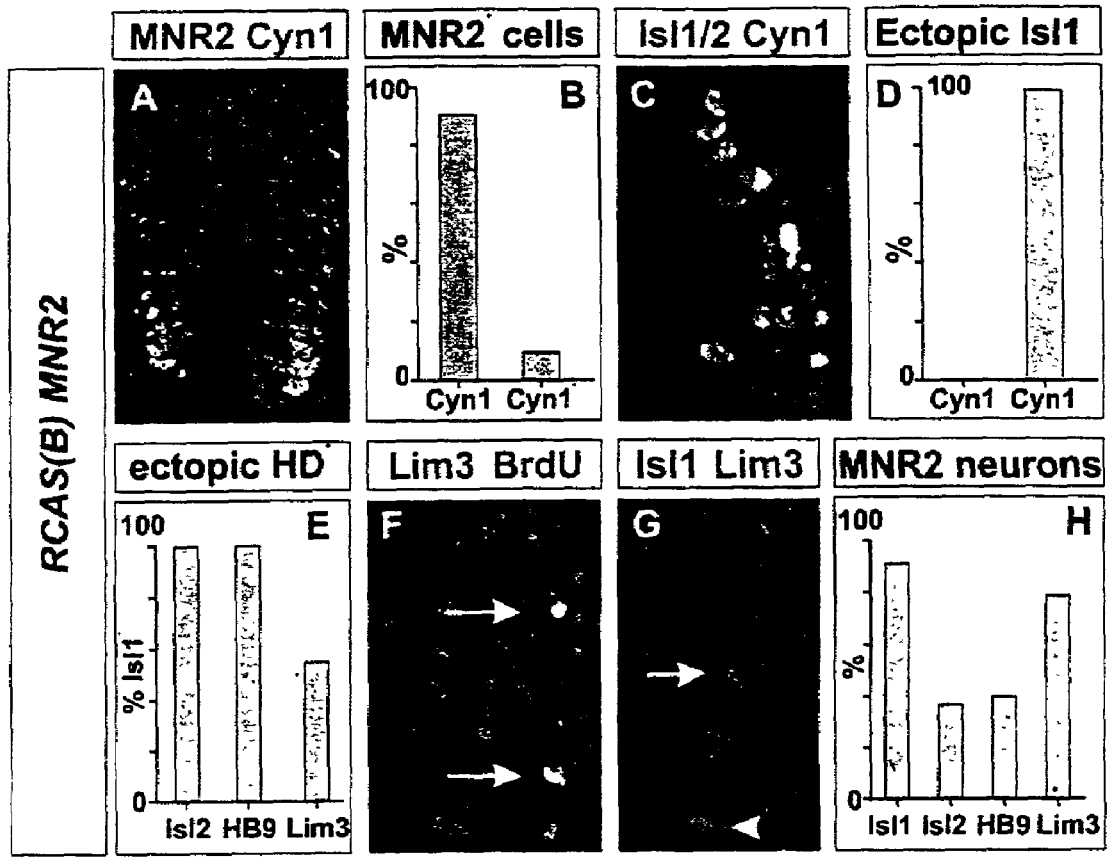
FIG. 4A  FIG. 4B  FIG. 4C  FIG. 4D
FIG. 4E  FIG. 4F  FIG. 4G  FIG. 4H
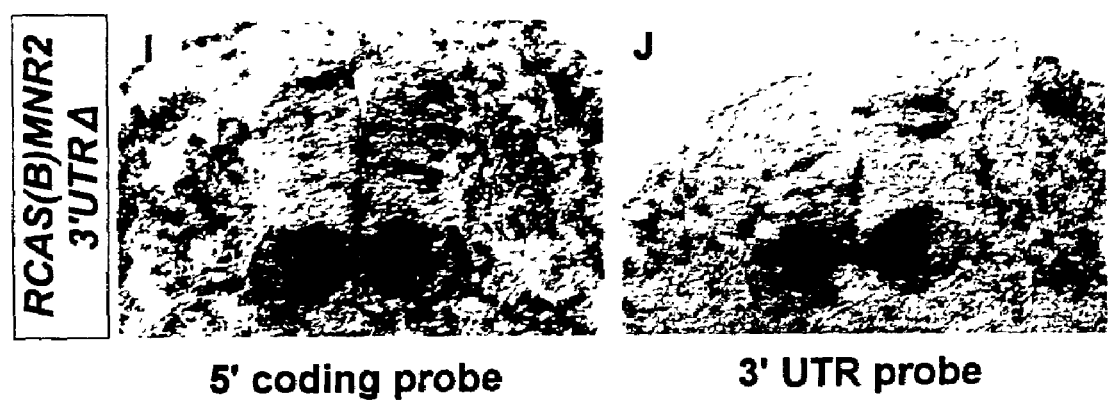
5' coding probe　　　　3' UTR probe
FIG. 4I　　　　　　　FIG. 4J

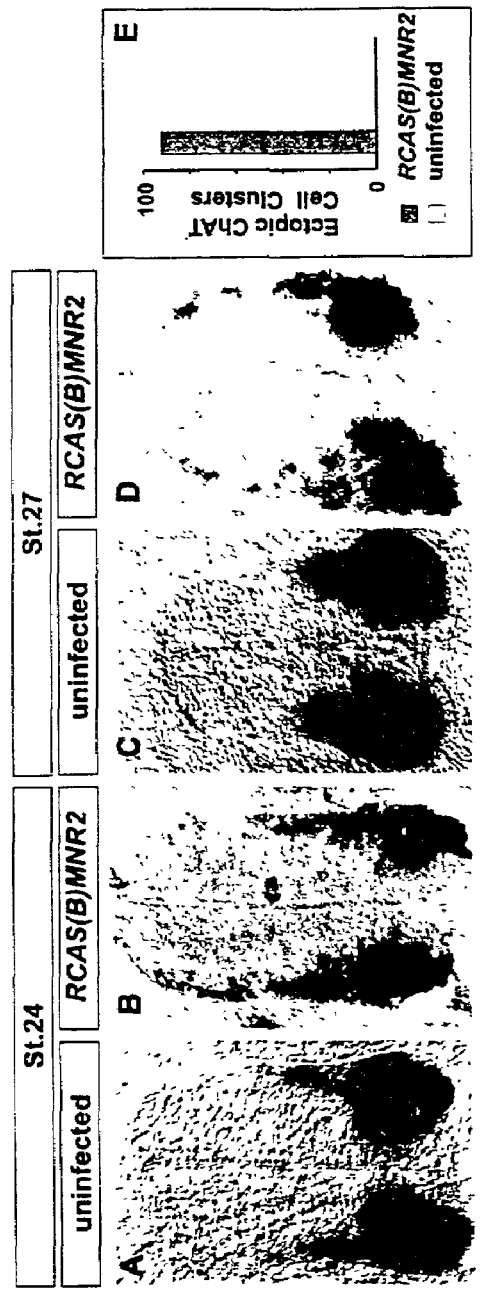
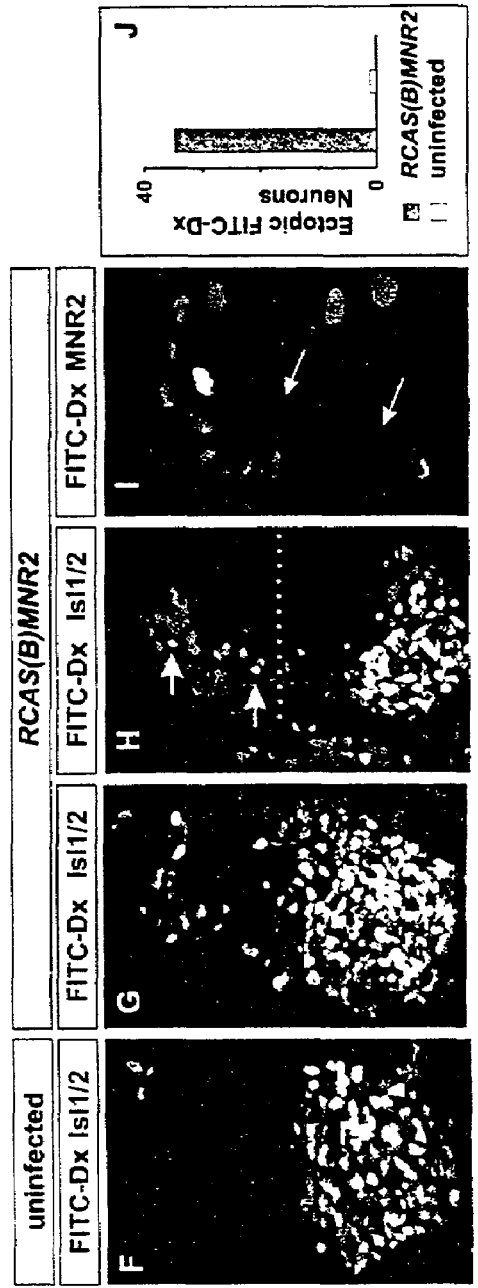
FIG. 5A  FIG. 5B  FIG. 5C  FIG. 5D  FIG. 5E
FIG. 5F  FIG. 5G  FIG. 5H  FIG. 5I  FIG. 5J

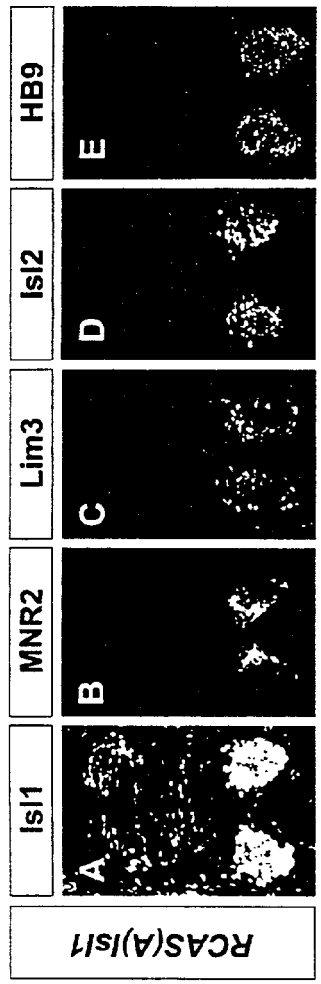
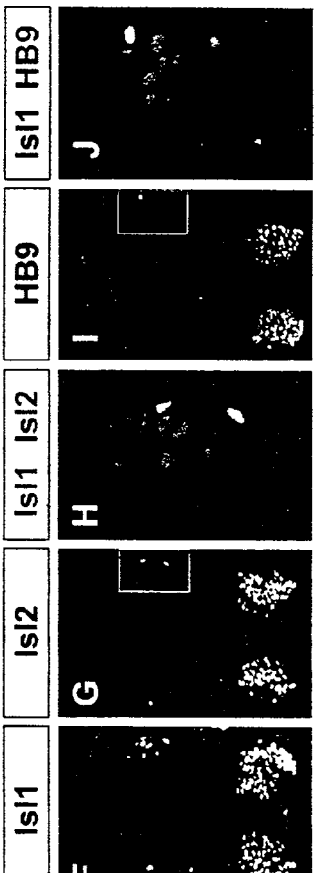
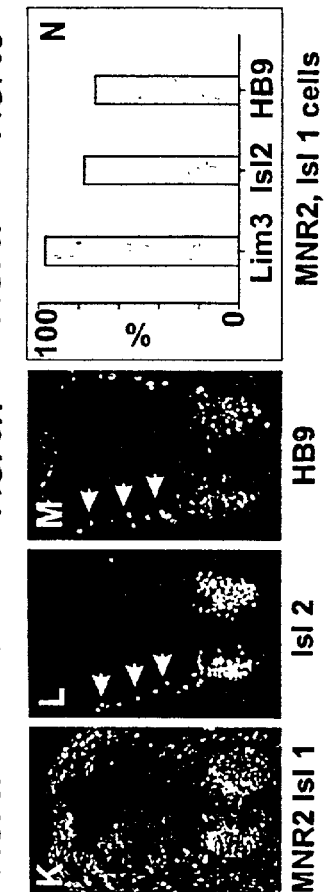

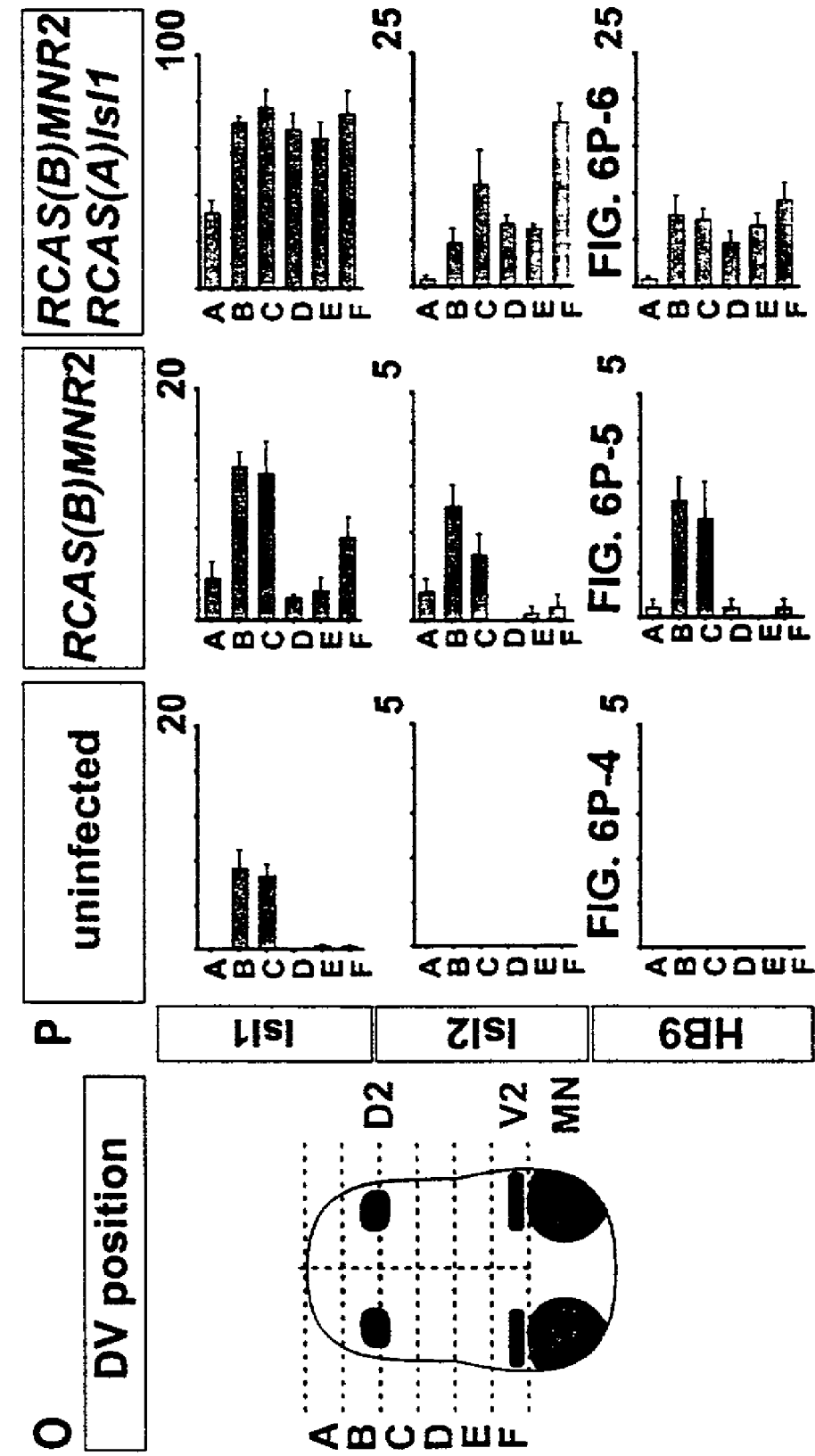

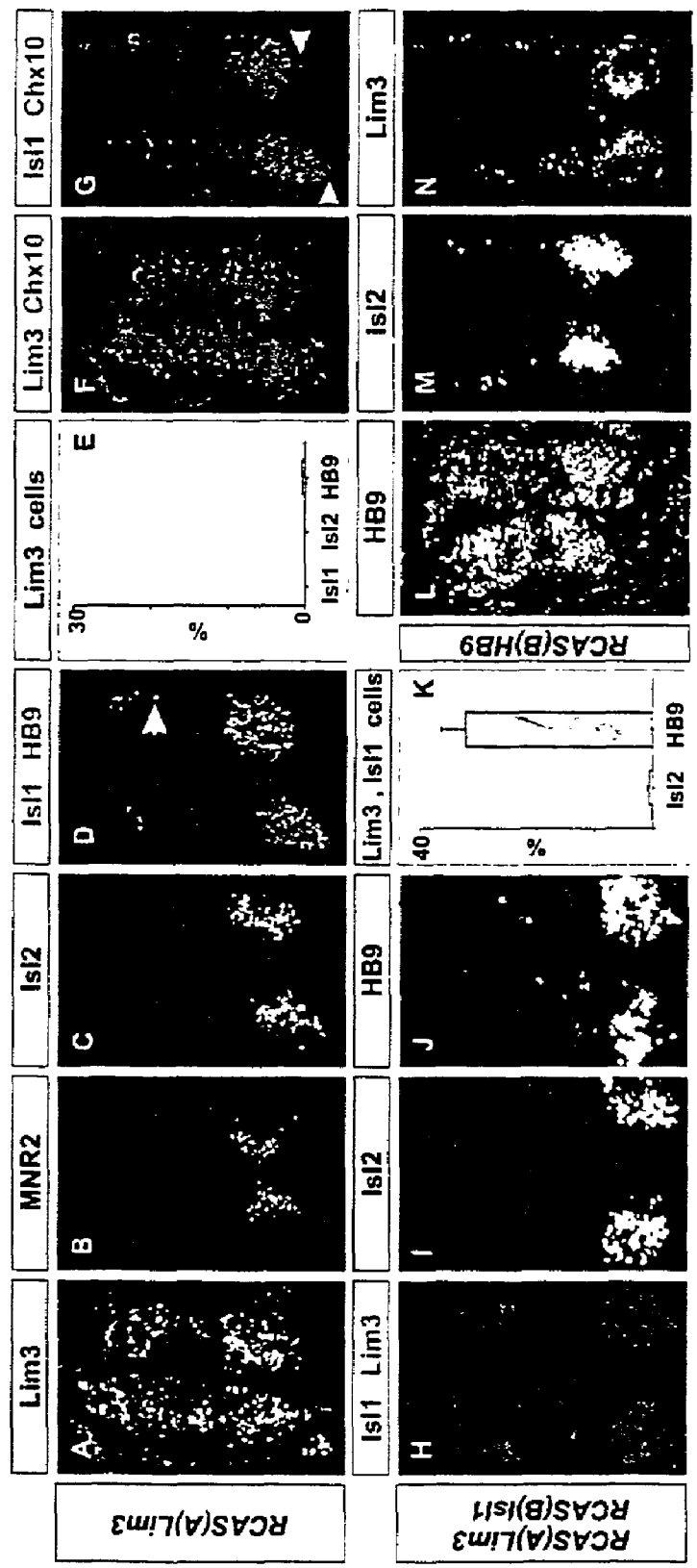

FIG. 9A  FIG. 9B
Interneuron Pattern  RCAS(B)MNR2
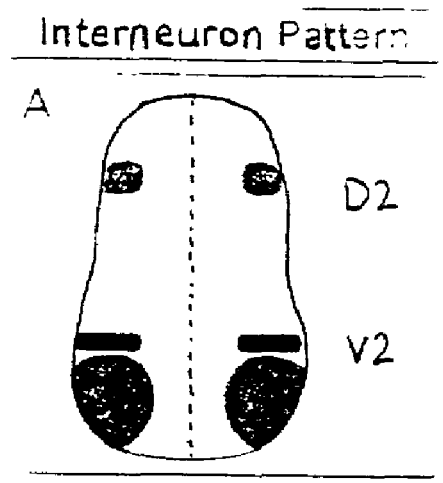
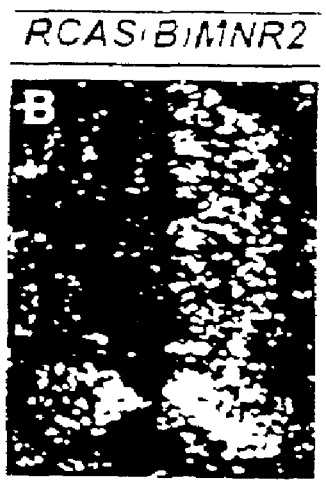
FIG. 9C  FIG. 9D  FIG. 9E
LH2  Isl1  LH2  Isl1
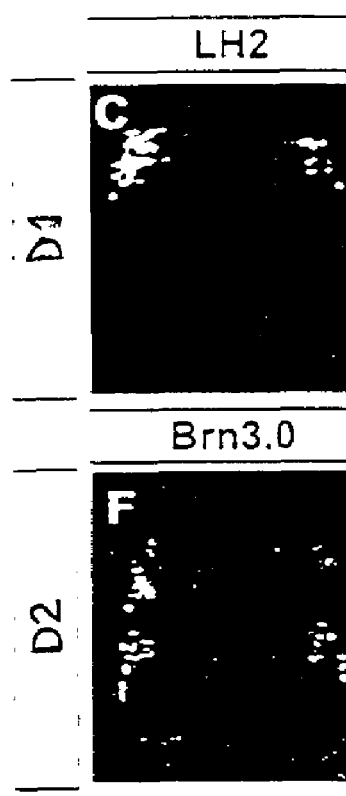 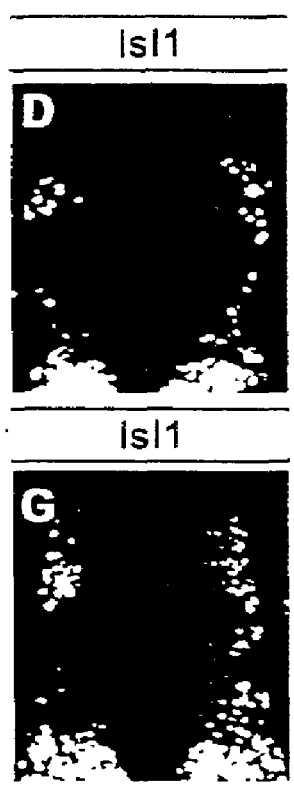 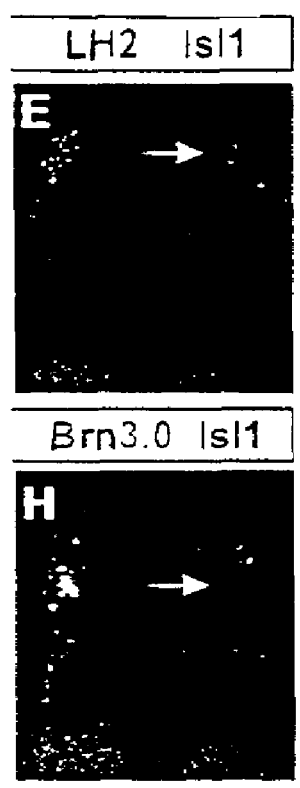
Brn3.0  Isl1  Brn3.0  Isl1
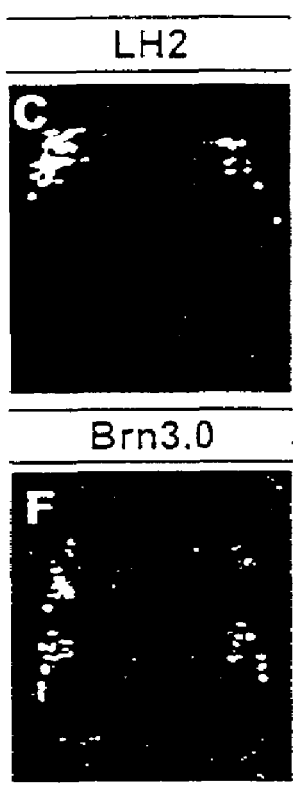 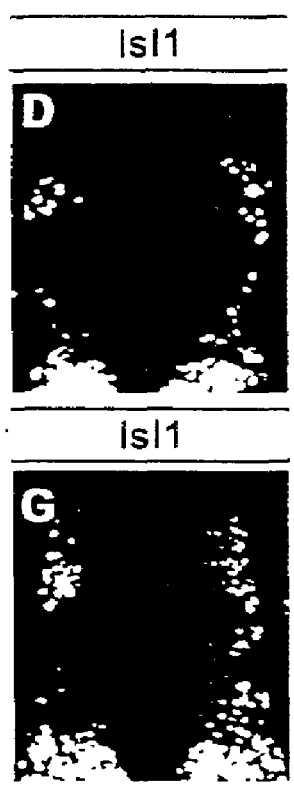 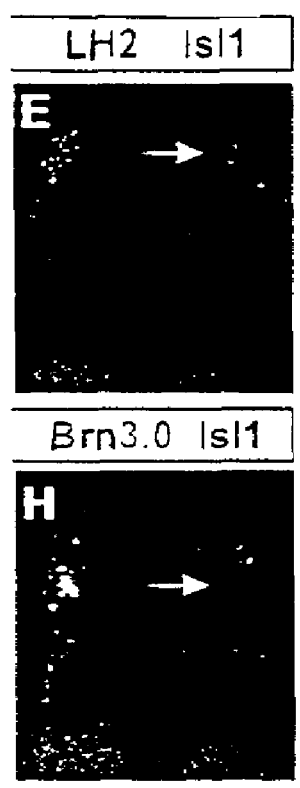
FIG. 9F  FIG. 9G  FIG. 9H

FIG. 10

SEQ. ID NO. 1 cMNR2-protein

```
  1  MHKPMEKSQN FRIEALLAEK PPRSASPPGL SPAGSPGPAG RTDTPSPRAP QAATPLGPAG
 61  FVPKPGLLHL PGPGLGTLPA LYPPAVYPLP ALGGQHAAFA YTAFPQLPPP GAEHLKAAVA
121  GSFPLEQWIR AGMLVPRLSD FHATPQSALM GKSRRPRTAF TSQQLLELEN QFKLNKYLSR
181  PKRFEVATSL MLTETQVKIW FQNRRMKWKR SRKAKEQGMA VEPEKPRGLG KADESLLPSQ
241  PQGQAGDSPE FVGCSPGTGF LCRSAELGYD PDSSCSGGEE DEEEEDDGMD TAERKMGSVL
```

FIG. 11   cMNR2-dna

SEQ. ID NO. 2

```
   1 CAGATCTGCT CCCAGATGCT CTGCCTCTCC TCGAAGGCCA GAGTCGGTGG GTCCGGGCCA
  61 GCTCTGCTCC TGCTCACCCG CCTGTCCCAG AGCAGCCAAG GCTTTCATCT CCACCTGTTT
 121 CTGGTGCCTT CACCTGGAGA AGACCAAACC GAGCAAATAA ATAACAATCT GCCCGTATGC
 181 ACCTGCTCCA TGGGCTTCTT GGGCGGATAG ACGATGCAGG GTTGTGGCCC CTGCGTGCAG
 241 CCAGCTCGGG CCCGCTGATG TCCCCGTGCC AAAGAGGTGC AAAGAGGAAC GGCACGGGGT
 301 GTGAAGAGCA GGATCGGGCC CCGGGTGTG CCGAGGGGCT GCGGAAGCCG GGGGAGGGAG
 361 GCCGGGCCGA CGGGGCGGGG GGCCGGCGGG GAGCCAATAG GGAGCTGGGG CAGGTGGAGG
 421 GGGGGGTTAA AACCCCCCG GTGGCGGCGG GCAAGCGAGT GCCCGGGAGG AGGAGCGGTG
 481 AGGAGGGCTG CCCCTGAGGG CAGCGGAGGC CGGCGCGCGC CCGCGAGTGA ATGCCCGCCG
 541 GTGCCGGGGT GGCCCGGGGC TGCCCGGCCG GGCGCTGCCC TGGCAGCCGA GCGGCGGGGG
 601 GAGGCACGCT GCGTTTTCGC GGGGCCCCGGC ACAAACCCAT GGAGAAGTCC
 661 CAAAACTTCC GCATCGAGGC GCTCCTGGCT GAGAAGCCGC CGCGGAGCGC CTCTCCTCCG
 721 GGGCTCAGCC CCGCGGGCAG CCCCGGCCCC GCCGGCCGTA CCGACACCCC CTCGCCTCGG
 781 GCTCCCCAGG CCGCCACCCC CCTCGGCCCG GCGGGCTTCG TCCCCAAACC CGGCTTGCTG
 841 CACCTCCCCG GCCCCGGGCT GGGCACCCTG GCCGGCCGC ACCCGCCTGC CGTGTACCCG
 901 CTGCCGGCCT TGGGGGGCCA GCACGCCGCT TTCGCCTACA CCGCCTTCCC CCAGCTGCCG
 961 CCGCCCGGCG CCGAGCACCT GAAGGCGGGG GTGGCCGGTT CCTTCCCGCT GGAGCAGTGG
1021 ATCCGAGCCG GGATGCTCGT GCCGAGGCTC TCCGACTTCC ACGCCACCCC ACAGTCCGCC
1081 TTGATGGGAA AGTCGCGCCG GCCCCGCACC GCCTTCACCA GCCAGCAGCT GCTGGAGCTG
1141 GAGAACCAGT TCAAGCTCAA CAAGTATCTG TCCAGGCCCA AGCGCTTCGA GGTGGCCACG
1201 TCGCTGATGC TCACTGAGAC GCAGGTGAAG ATCTGGTTCC AGAACCGCCG CATGAAGTGG
1261 AAGCGGAGCC GCAAAGCCAA GGAGCAGGGG ATGGCAGTGG AGCCCGAGAA GCCACGGGGG
1321 CTTGGCAAAG CTGATGAGAG TCTGCTGCCC AGCCAGCCCC AGGGACAGGC TGGTGACAGC
1381 CCCGAGTTTG TGGGGTGCAG CCCCGGAACG GGCTTCCTGT GCCGCAGCGC CGAGCTGGGC
1441 TATGACCCGG ACTCCTCCTG TTCAGGGGGA GAGGAGGATG AGGAAGAGGA GGACGATGGG
1501 ATGGACACTG CGGAGAGGAA GATGGCTCT GTGTTGTGAA GAGGTTCCCG GGTGAGGAGT
1561 TGGACCAGTC TCGGCTGGCA GACACAGACT GTGCCCATGT GCCGCAGCGC GGCTGAGGGG
1621 AGCCTGCCCC CCCCCTCCTT TAACTTATGT GTGTTTGGAG TCTATTTAAT GTGTAATTAT
1681 TCCTGTGTGT ATCTTGGGGT TTCCCACAT CCCTCCCCTA TAAAGCTGTT ATCCGG
```

FIG. 12

SEQ. ID NO. 3 cHB9-protein

```
  1 MEKSKNFRID ALLAVDPPKA AAQSAPLALV TGGSGGGSPP SSSSSSSSSS SSSSELPADC
 61 PRTDSPSPPR LLPAHCALLP KAAFLGGGGP GGGHPQHHAL GLHPAGPGGP GLYGHPVYGY
121 PALGGQHPAL SYSYSQVQGA HPAHPSADPI KLSAGTFQLD QWLRASTAGM ILPKMPDFGS
181 QAQSNLLGKC RRPRTAFTSQ QLLELEHQFK LNKYLSRPKR FEVATSLMLT ETQVKIWFQN
241 RRMKWKRQKK AKEQAAQEAE NEKGGGGGED KSGPRELLLP GPEKGGGRRL RELPDSEPED
301 EEEEEEEEE AEAGRCCPYH SSDCSEADEE DSQSGGRPGA PPPPAQPQ*
```

FIG. 13
SEQ. ID NO. 4 cHB9-DNA

```
   1 CCGGGCTGGC CTCTCGCCGC CTCCGCCGCT CCCATGGAAA AATCCAAAAA TTTCCGCATC
  61 GACGCGCTGC TGGCTGTCGA TCCCCCCAAG GCGGCGGGCGC AGAGCGCTCC GCTGGCCCTG
 121 GTCACCGGCG GCTCCGGCGG CGGCAGCCCT CCGTCTTCGT CGTCCTCCTC GTCGTCGTCG
 181 TCCTCCTCTT CTTCCGAGCT CCCCGCCGAC TGCCCGCGCA CCGACAGCCC CTCTCCGCCT
 241 CGCCTGCTGC CCGGCACTG CGCGCTGCTG CCCAAAGCCG CCTTCCTGGG CGGGGGGGA
 301 CCCGGGGGCG GCCACCCGCA GCACCACGCC CTGGGCTGC ACCCGCGGG GCCGGGCGGG
 361 CCGGGGCCTCT ACGGGCACCC GGTGTACGGC TACCCGGCGT TGGGCGGGCA GCACCCGGCG
 421 CTCTCCTATT CCTATTCGCA AGTGCAGGGA GCGCACCCCG CGCATCCCTC CGCCGACCCC
 481 ATCAAGCTGA GCGCCGGCAC CTTTCAGCTG GACCAGTGGC TGCGGGCGAG CACGGCCGGC
 541 ATGATCCTGC CCAAAATGCC CGACTTCGGC TCTCAGGCGC AGTCCAACCT GCTGGGGAAG
 601 TGCCGGCGGC CCGCACCGC CTTCACCAGC CAGCAGCTGC TGGAGCTGGA GCACCAGTTC
 661 AAACTCAACA AGTACCTCTC CCGGCCCAAG CGCTTCGAGG TGGCCACGTC GCTGATGCTC
 721 ACCGAGACGC AGTGTGAAGAT TTGGTTCCAG AACCGCCGCA TGAAATGGAA GCGCCAGAAA
 781 AAGGCGAAGG AGCAGGCGGC GCAGGAGGCA GAGAACGAGA AAGGAGGAGG AGGAGGAGAG
 841 GACAAAAGCG GGCCGAGGGA ACTGCTGCTG CCCGGCCCGG AGAAAGGCGG CGGGAGGCGG
 901 CTGAGGGAGC TGCCCGACAG CGAGCCCGAG GACGAGGAGG AGGAAGAAGA GGAGGAAGAG
 961 GAGGCCGAGG CCGGGCGGTG CTGCCCCTAC CACTCCTCCG ACTGCTCCGA GGCGGACGAG
1021 GAGGACTCGC AGTCCGGAGG ACGGCCCGGA GCCCCCCGC CACCCCCCGC ACAGCCGCAC
1081 TGAGCCCACG GCCGCCCCGT CGGGGCCCCC CCGGCCTCCTG GAGCCTCCTG GCCCCGCTCT
1141 CCATCCCGCT CTCCCATCCC TCCCTGCTCG GAGGGGACG CGGAAAGGGA TCTCCCGTCT
1201 GCCGAGCGGG AGGGAGGATT CACACAGTGT TATTATTGAC TGAGAAGCGG CCACGACTTG
1261 AGCCCCCCTC CCCGCCCCGC CCTATCGGAA CCGTTTCCTT CTTACCATAT ATCGGGAAAA
1321 GTGTTTATGT CATGAACGTT AAAAAAGGCA AAATGAATTC CAGATCTCAA TACTGTCTTT ATTTTGTATA
1381 TCCTATTTAT AAAAAAGGCA AAATGAATTC CTCTACTTAT GCATGCTAAA TTATTACCCA
1441 GCCCCTTCCG CCTGAGGTGG GGGGAGGAA TATAAATAAA GAGCGTTTTG TACTGTGAAA
1501 AAAAAAAAAA AAAA
```

GENE ENCODING MNR2 AND USES THEREOF

This application is a divisional of U.S. Ser. No. 09/162,524, filed Sep. 29, 1998, now U.S. Pat. No. 6,387,656 B1, issued May 14, 2002, the contents of which are hereby incorporated by reference into the present application.

The invention disclosed herein was made with support under National Institute of Health training grant No. 5T32GM07367, U.S. Department of Health and Human Services. Accordingly, the United States Government has certain rights in this invention.

Throughout this application various publications are referred to within parenthesis. Full citations for these publications may be found at the end of the specification immediately preceding the claims. The disclosures of these publications, in their entireties, are hereby incorporated by reference into this application in order to more fully describe the state of the art to which this invention pertains.

BACKGROUND OF THE INVENTION

Sonic hedgehog signaling controls the differentiation of motor neurons in the ventral neural tube but the intervening steps are poorly understood. A differential screen of a cDNA library derived from a single Shh-induced motor neuron has identified a novel homeobox gene, MNR2, expressed by motor neuron progenitors and transiently by post-mitotic motor neurons. The ectopic expression of MNR2 in neural cells initiates a program of somatic motor neuron differentiation characterized by the expression of homeodomain proteins, by neurotransmitter phenotype and by axonal trajectory. Our results suggest that the Shh-mediated induction of a single transcription factor, MNR2, is sufficient to direct somatic motor neuron differentiation.

The assembly of neural circuits in the vertebrate central nervous system (CNS) is initiated by the generation of distinct classes of neurons at characteristic positions. The specification of neuronal identity in the CNS appears to be controlled by inductive signals secreted by embryonic organizing centers (Lumsden and Krumlauf, 1996; Tanabe and Jessell, 1996). These signals appear to define neuronal fates by regulating the expression of cell-intrinsic determinants, many of which are transcription factors (Bang and Goulding, 1996). However, the pathways by which specific inductive signals determine the fate of individual neuronal cell types in the CNS are poorly defined. As a consequence, it is unclear whether there are individual transcription factors assigned, in a dedicated manner, to the specification of particular neuronal subtypes or whether the parallel actions of several factors are required.

Spinal motor neurons constitute one subclass of CNS neuron for which some early differentiation steps have been defined (Pfaff and Kintner, 1998). The differentiation of motor neurons depends on spatial signals provided by Sonic Hedgehog (Shh) secreted from the notochord and floor plate (Marti et al. 1995; Roelink et al., 1995; Tanabe et al., 1995; Chiang et al. 1996; Ericson et al. 1996). Shh acts initially to convert medial neural plate cells into a population of ventral progenitors (Ericson et al., 1996) and later directs the differentiation of ventral progenitors into motor neurons and interneurons at distinct concentration thresholds (Roelink et al. 1995; Ericson et al., 1997). The Shh-induced pathway of motor neuron differentiation appears, however, to operate within the context of an independent program of neurogenesis. Neural progenitors that have been exposed to Shh undergo two or more cell divisions before leaving the cell cycle and acquiring motor neuron properties (Ericson et al., 1996). Over this period, ventral progenitors require continued Shh signaling, achieving Shh-independence and committing to a motor neuron fate only late in their final division cycle (Ericson et al., 1996).

Cells in the ventral neural tube respond to graded Shh signaling with the establishment of distinct ventral progenitor populations defined by the expression of the homeodomain proteins Pax6 and Nkx2.2 (Ericson et al., 1997). These two progenitor populations generate distinct classes of motor neurons. Pax6$^+$ progenitors give rise to somatic motor neurons whereas Nkx2.2$^+$ progenitors generate visceral motor neurons (Ericson et al. 1997). As these two progenitor populations leave the cell cycle they express different homeodomain proteins that characterize distinct motor neuron subtypes (Tsuchida et al., 1994; Varela-Echavarria et al., 1996; Ericson et al., 1997; Pattyn et al. 1997). The activity of Pax6 is necessary for the differentiation of somatic motor neurons within the hindbrain (Ericson et al., 1997; Osumi et al., 1997) but it appears that its function is indirect, being required to repress the expression of Nkx2.2 (Ericson et al., 1997).

The dispensibility of Pax6 for somatic motor neuron generation implies the existence of additional genes that determine somatic motor neuron identity. Moreover, the late commitment of progenitors to a somatic motor neuron fate suggests that the onset of expression of such genes occurs only during the final division cycle of motor neuron progenitors. To identify such determinants a screen for genes expressed by somatic motor neuron progenitors was performed and described, here is the characterization of a novel homeobox gene, MNR2.

MNR2 is expressed selectively by Pax6$^+$ motor neuron progenitors and persists transiently in post-mitotic somatic motor neurons. The ectopic expression of MNR2 in vivo is sufficient to activate a program of somatic motor neuron differentiation characterized by the expression of several homeodomain proteins and *Choline Acetyltransferase* (ChAT), by the autoactivation of MNR2 and by the extension of axons into ventral roots. This program of motor neuron differentiation is accompanied by the repression of spinal interneuron fates. Thus, the Shh-triggered differentiation of ventral progenitor cells into somatic motor neurons may be directed by the expression of a single homeodomain protein, MNR2.

This invention provides an isolated nucleic molecule encoding a motor neuron restricted MNR2, protein that has the capacity to induce motor neuron generation.

SUMMARY OF THE INVENTION

This invention provides an isolated nucleic molecule encoding a motor neuron restricted pattern, MNR2, protein.

This invention provides a vector which comprises the isolated nucleic acid encoding a motor neuron restricted pattern, MNR2, protein.

This invention provides a host cell containing the vector which comprises the isolated nucleic acid encoding a motor neuron restricted pattern, MNR2, protein.

This invention provides a method of producing a polypeptide having the biological activity of a mammalian MNR2 which comprises growing host cells selected from a group consisting of bacterial, plant, insect or mammalian cell, under suitable conditions permitting production of the polypeptide.

This invention provides an isolated nucleic acid molecule of at least 15 contiguous nucleotides capable of specifically hybridizing with a unique sequence included within the sequence of the nucleic acid molecule encoding a motor neuron restricted pattern, MNR2, protein.

This invention provides an antisense oligonucleotide having a nucleic acid sequence capable of specifically hybridizing to an mRNA molecule encoding a MNR2 protein.

This invention provides a monoclonal antibody directed to an epitope of an MNR2 protein.

This invention provides a purified MNR2 protein.

This invention provides a method of inducing differentiation somatic motor neurons which comprises expressing MNR2 protein in neural progenitor cells.

This invention provides a transgenic nonhuman mammal which comprises an isolated nucleic acid encoding a motor neuron restricted pattern, MNR2, protein, is a DNA molecule.

This invention provides a method of determining physiological effects of expressing varying levels of MNR2 protein in a transgenic nonhuman mammal which comprises producing a panel of transgenic nonhuman animals, each a transgenic nonhuman mammal, each nonhuman mammal expressing a different amount of MNR2 protein.

This invention provides a method of producing an isolated purified MNR2 protein which comprises: a) inserting a nucleic acid molecule encoding a MNR2 protein into a suitable vector; b) introducing the resulting vector into a suitable host cell; c) selecting the introduced host cell for the expression of the MNR2 protein; d) culturing the selected cell to produce the MNR2 protein; and e) recovering the MNR2 protein produced.

This invention provides a method of inducing differentiation of somatic motor neurons in a subject comprising administering to the subject the purified MNR2 protein in an amount effective to induce differentiation of somatic motor neurons in the subject.

This invention provides a pharmaceutical composition comprising a purified MNR2 protein and a pharmaceutically acceptable carrier.

This invention provides a method for treating a subject afflicted with an abnormality associated with a lack of one or more normally functioning motor neurons which comprises introducing an amount of a pharmaceutical composition comprising a purified MNR2 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

This invention provides a method of treating a subject afflicted with a neurodegenerative disease which comprises introducing an amount of a pharmaceutical composition which comprises a purified MNR2 protein and a pharmaceutically acceptable carrier effective to generate somatic motor neurons from undifferentiated precursor motor neuron cells in the subject, thereby treating the subject afflicted with the neurodegenerative disease.

This invention provides for a method of treating a subject afflicted with an acute nervous system injury which comprises introducing an amount of a pharmaceutical composition which comprises a purified MNR2 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury, wherein the acute nervous system injury is localized to a specific central axon which comprises surgical implantation of a pharmaceutical composition comprising a MNR2 protein and a pharmaceutically acceptable carrier effective to generate motor neurons from undifferentiated precursor motor neuron cells located proximal to the specific central axon, so as to alleviate the acute nervous system injury localized to a specific central axons thereby treating the subject afflicted with the acute nervous system injury.

This invention provides a method for diagnosing a chronic neurodegenerative disease associated with the expression of a MNR2 protein in a sample from a subject which comprises: (a) obtaining DNA from the sample of the subject suffering from the chronic neurodegenerative disease; (b) performing a restriction digest of the DNA with a panel of restriction enzymes; (c) separating the resulting DNA fragments by size fractionation; (d) contacting the resulting DNA fragments with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; (e) detecting labeled bands which have hybridized to the nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence to create a unique band pattern specific to the DNA of subjects suffering from the chronic neurodegenerative disease; (f) preparing DNA obtained from a sample of a subject for diagnosis by steps (a–e); and (g) comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a MNR2 protein in a sample from a subject which comprises: (a) obtaining RNA from the sample of the subject suffering from chronic neurodegenerative disease; (b) separating the RNA sample by size fractionation; (c) contacting the resulting RNA species with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; (d) detecting labeled bands which have hybridized to the RNA species to create a unique band pattern specific to the RNA of subjects suffering from the chronic neurodegenerative disease; (e) preparing RNA obtained from a sample of a subject for diagnosis by steps (a–d); and (f) comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease if the patterns are the same.

This invention provides a functionally equivalent analog of MNR2 that induces MNR2 differentiation of neural progenitor cells.

This invention provides a functionally equivalent analog of MNR2 that prevents MNR2 differentiation of neural progenitor cells.

This invention provides a method of treating a subject afflicted with a neuromuscular disease which comprises introducing an amount of a pharmaceutical composition comprising a purified MNR2 protein and a pharmaceutically acceptable carrier effective to activate acetylcholine to activate muscle cells.

BRIEF DESCRIPTION OF THE FIGURES

FIGS. 1A–H.

Figure 8:
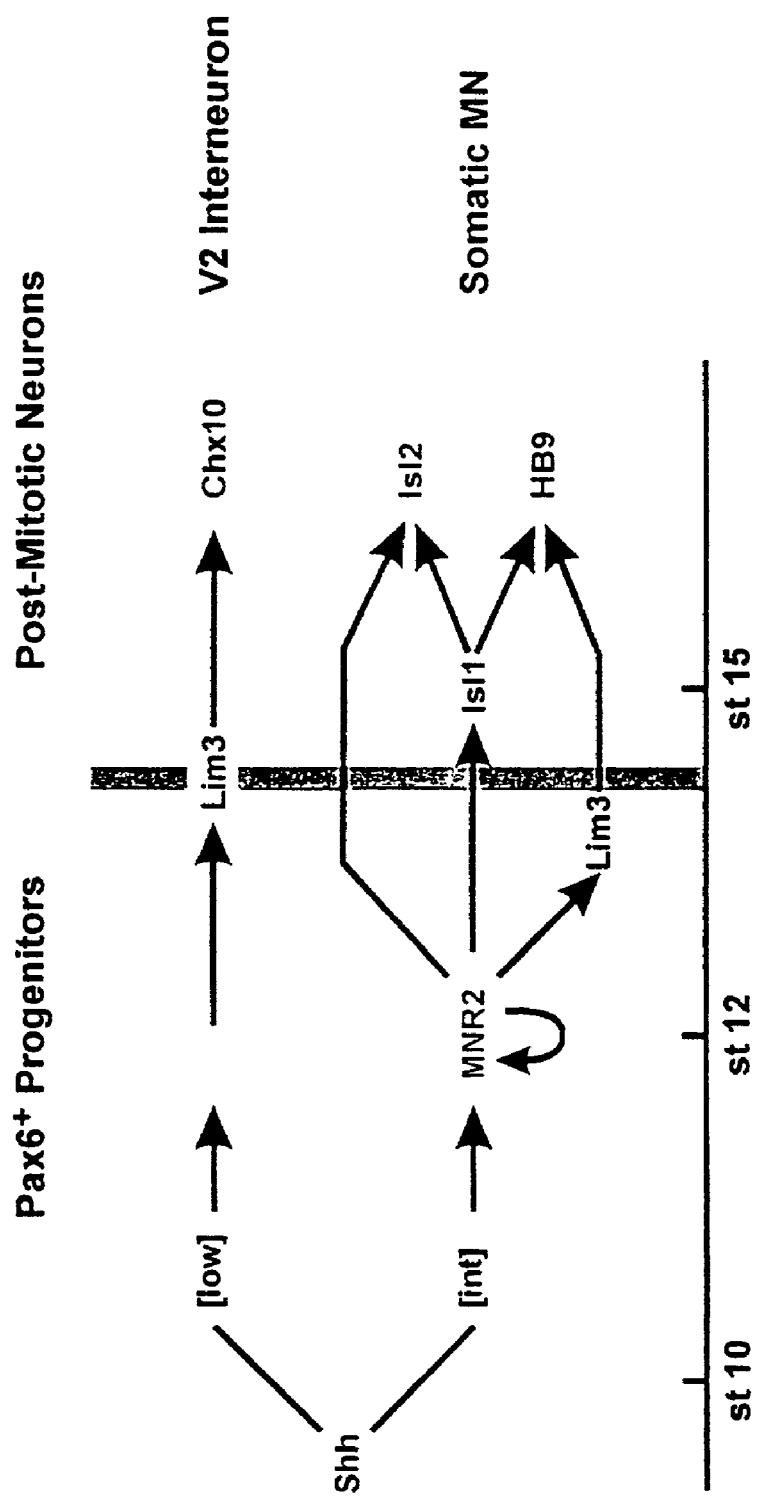

Isolation and Characterization of MNR2.

FIG. 1A.

Hybridization analysis of cells isolated from [i] explants grown alone or with Shh. Left hand panels show cells isolated from explants grown with 2 nM Shh and right hand panels show cells isolated from explants grown without Shh. Top panels: ethidium labeling of PCR-amplified single cell-derived cDNAs. Lower panels: specific PCR-amplified transcripts in individual cells. Solid circle indicates a motor neuron defined by Isl1, HB9 and Isl2 expression. Open circles indicate interneurons, defined by Lim2 expression.

FIG. 1B.

Sequence similarity of the chick and human HB9 proteins and chick MNR2 and HB9 proteins Conservation is indicated by higher similarity scores, using the PileUp and PlotSimilarity programs, Wisconsin Package 9.1, Genetics Computer Group. Chick MNR2 is 56% identical to chick HB9. Chick HB9 is 77% identical to human HB9. HD: homeodomain.

FIGS. 1C and 1D.

MNR2 expression in sections of cervical spinal cord of stage 12 FIG. 1C. and stage 16 FIG. 1D. embryos.

FIG. 1E.

MNR2 expression in a stage 20 embryo. White circle shows position of the otic vesicle. Arrow indicates expression of MNR2 in abducens motor neurons.

FIGS. 1F–H.

Induction of MNR2 expression by Shh. [i] explants grown alone for 24 h do not give rise to MNR2$^+$ cells FIG. 1F. [i] explants grown with Shh (4 nM) for 24 h contain many MNR2$^+$ cells FIG. 1G not all of which express Isl1/2 FIG. 1H. Images representative of 4 explants.

FIGS. 2A–K.

Expression of MNR2 Precedes that of Other Homeodomain Proteins.

FIG. 2A.

MNR2 expression in the ventral neural tube of a stage 18 embryo labeled with a pulse of BrdU. Many cells coexpress MNR2 and BrdU.

FIG. 2B.

Adjacent section to FIG. 2A. showing that Isl1/2$^+$ cells do not coexpress BrdU.

FIG. 2C.

Coexpression of MNR2 and MPM2 (Westendorf et al., 1994) in a cell (arrow) in the ventral neural tube. Approximately one MNR2$^+$, MPM2 cell was detected/10 μm section, analysis of 300 MNR2$^+$ cells in 30 sections.

FIG. 2D

Coexpression of MNR2 and Pax6 by ventral cells in stage 20 spinal cord.

FIG. 2E.

MNR2$^+$ cells located dorsal to Nkx2.2$^+$ cells in stage 20 chick spinal cord.

FIG. 2F.

MNR2 expression in the caudal hindbrain (r7/r8) is restricted to dorsal hypoglossal (somatic) motor neurons. Ventral vagal (visceral) motor neurons express Isl1 but not MNR2. MNR2 is absent from other cranial motor neurons and from thoracic visceral motor neurons. MNR2 expression is excluded from oculomotor and trochlear motor neurons, consistent with their expression of the visceral motor neuron markers Phox2a and Phox2b (Pattyn et al., 1997).

FIGS. 2G–J.

Expression of MNR2 and other homeodomain protein markers of spinal motor neurons in stage 20 embryos. Arrow in FIG. 2G. indicates dorsal Isl1$^+$ (D2) neurons. Lim3 cells dorsal to MNR2$^+$ cells in FIG. 2J. are V2 neurons (arrow).

FIG. 2K.

Temporal sequence of homeodomain protein expression by somatic motor neuron progenitors and newly-differentiated somatic motor neurons. D2 and V2 neuron domains are shown. Dotted line indicates cell cycle exit.

FIGS. 3A–J.

MNR2 Induces Somatic Motor Neuron Transcription Factors.

FIG. 3A.

Sections of the spinal cord of an MNR2-infected embryo at stage 23. In this embryo, ectopic MNR2 expression is detected predominantly on the right side.

FIGS. 3B–E.

Ectopic expression of Isl1 FIG. 3B. Isl2 FIG. 3C. HB9 FIG. 3D. and Lim3 FIG. 3E. in an MNR2-infected embryo. Ectopic cells exhibit no dorsoventral (DV) restriction. The increase in the number of dorsal Isl1$^+$ cells FIG. 3B. is not caused by the precocious differentiation of D2 neurons (data not shown).

FIG. 3F

Detail of an MNR2-infected spinal cord showing that ectopic Isl1$^+$ cells coexpress MNR2. Similar findings were obtained for Isl2$^+$ and HB9$^+$ cells.

FIG. 3G.

Section through the spinal cord of an MNR2-infected embryo showing Pax7$^+$ dorsal progenitors. Ectopic MNR2 does not repress Pax7. Lateral MNR2$^+$, Pax7$^-$ cells are post-mitotic neurons. Arrowhead indicates DV boundary.

FIGS. 3H–J.

Induction of Isl1/2 in ventral progenitors by MNR2. [i] explants isolated from MNR2-infected embryos and grown in vitro for 24 h with 0.5 nM Shh contain many MNR2$^+$ cells FIG. 3H. Many of these cells express Isl1/2 FIG. 3I. [i] explants isolated from uninfected embryos and exposed to 0.5 nM Shh do not contain MNR2$^+$ cells FIG. 3J. and do not give rise to Isl1/2$^+$ neurons (data not shown). Similar results obtained in 4 explants.

FIGS. 4A–J.

MNR2 Functions Within the Context of a General Neurogenic Program.

FIG. 4A.

Coexpression of MNR2 and Cyn1 in the spinal cord of an MNR2-infected embryo, analyzed at stage 21. Cyn1$^+$, MNR2$^+$ cells are restricted to the lateral margin of the spinal cord. MNR2 expression does not alter the number of Cyn1$^+$ cells.

FIG. 4B.

Quantitative analysis of Cyn1 expression by ectopic MNR2$^+$ cells. Similar values were obtained from stages 20–23. Analysis derived from >300 MNR2$^+$ cells.

FIG. 4C.

Detail of the dorsal spinal cord of an MNR2-infected embryo. All ectopic Isl1/2$^+$ cells coexpress Cyn1.

FIG. 4D.

MNR2-induced ectopic Isl1$^+$ cells coexpress Cyn1. Analysis of >200 ectopic Isl1$^+$ cells.

FIG. 4E.

Proportion of MNR2-induced ectopic Isl2$^+$, HB9$^+$ and Lim3$^+$ cells that coexpress Isl1. All Isl2$^+$ and HB9$^+$ cells coexpress Isl1. Only 55% of ectopic Lim3$^+$ cells coexpress Isl1. Analysis of 77 Isl2$^+$, 38 HB9$^+$ and 96 Lim3$^+$ cells.

FIG. 4F.

Many ectopic Lim3$^+$ cells in MNR2-infected embryos are labeled (arrows) by a BrdU pulse.

FIG. 4G.

Detail showing that many MNR2-induced ectopic Lim3$^+$ cells do not express Isl1.

FIG. 4H.

Expression of homeodomain protein markers in ectopic MNR2$^+$ neurons (MNR2$^+$/Cyn1$^+$ cells). Analysis of 690 Isl1$^+$, 70 Isl2$^+$, 111 HB9$^+$ and 540 Lim3$^+$ cells. More than 2000 MNR2$^+$ cells analyzed from more than 40 MNR2-infected embryos.

FIG. 4I.

Misexpression of MNR2 in an embryo infected with a MNR2 3'Δ construct. Section labeled with a 5' coding probe.

FIG. 4J.

Activation of endogenous MNR2 in an MNR2-infected embryo revealed using a 3' non-coding probe. The endogenous MNR2 gene is activated both in neural and surrounding tissues.

FIGS. 5A–J.

MNR2 Induces Later Features of the Somatic Motor Neuron Phenotype.

FIGS. 5A–D.

ChAT expression in the spinal cord of uninfected FIG. 5A. and FIG. 5C. and MNR2-infected embryos FIGS. 5B. and D. Ectopic clusters of ChAT$^+$ cells are detected in the dorsal spinal cord of MNR2-infected embryos (arrows in FIGS. 5 B and D).

FIG. 5E.

Quantitation of ectopic dorsal ChAT$^+$ cell clusters in uninfected and MNR2-infected embryos. Number of ectopic dorsal ChAT$^+$ cell clusters detected in 70, 15 μm sections.

FIGS. 5F–H.

FITC-Dextran$^+$ (FITC-Dx) labeled neurons in the spinal cord of stage 25 embryos after application of FITC-Dx to the ventral roots. In uninfected embryos FIG. 5F., retrogradely labeled cells are restricted to Isl1/2$^+$ motor neurons. In MNR2-infected embryos ectopic FITC-Dx$^+$ Isl1/2 are detected in the V1 and V2 neuron domain FIG. 5G. Ectopic FITC-Dx$^+$ neurons are also located in the dorsal spinal cord and coexpress Isl1/2 FIG. 5H and MNR2 FIG. 5I. The axons of these neurons project ventrally (arrows in FIG. 5I). Sensory axons in the dorsal root entry zone have also been labeled in some embryos (see FIG. 5I).

FIG. 5J.

Ectopic FITC-Dx$^+$ neurons in the dorsal spinal cord (DV boundary is shown by dotted line in FIG. 5H., analyzed in 80, 10 μm sections of uninfected and MNR2-infected embryos. Ectopic FITC-Dx neurons in the V1 and V2 neuron domain are not plotted in FIG. 5J.

FIGS. 6A–P.

Cooperation of MNR2 and Isl1 in the Induction of Somatic Motor Neurons.

FIGS. 6A–E.

Sections of the spinal cord of an embryo infected with Isl1 virus and analyzed at stage 20. Despite ectopic expression of Isl1 FIG. 6A., no ectopic MNR2$^+$ FIG. 6B., Lim3$^+$ FIG. 6C., Isl2$^+$ FIG. 6D. or HB9$^+$ FIG. 6E. cells are detected. Images representative of six infected embryos.

FIGS. 6F–H.

Isl1, Isl2 and HB9 expression in an MNR2-infected embryo analyzed at stage 20. Most Isl1$^+$ neurons are focused on the D2 neuron domain although more ventrally located neurons are also detected FIG. 6F. All Isl2$^+$ cells FIG. 6G. coexpress Isl1 FIG. 6H. (see panel FIG. 6P. for quantitation).

FIG. 6I, 6J.

HB9 expression in a stage 20 MNR2-infected embryo. All ectopic HB9$^+$ cells FIG. 6I. coexpress Isl1 FIG. 6J. See panel FIG. 6P. for quantitation.

FIGS. 6K–M.

Isl2 and HB9 expression in the spinal cord of an embryo coinfected with MNR2 and Isl1 viruses, analyzed at stage 20.

FIG. 6K.

Many ectopic MNR2$^+$ cells coexpress Isl1.

FIG. 6L.

Ectopic expression of Isl2 in the spinal cord of an embryo coinfected with MNR2 and Isl1 viruses, analyzed at stage 20.

FIG. 6M.

Ectopic expression of HB9 in the spinal cord of an embryo coinfected with MNR2 and Isl1 viruses, analyzed at stage 20.

FIG. 6N.

Expression of Lim3, Isl2 and HB9 in ectopic MNR2$^+$, Isl1$^+$ cells. Analysis of more than 300 cells for each marker, from four infected embryos.

FIGS. 6O. and P.

Distribution of ectopic Isl1$^+$, Isl2$^+$ and HB9$^+$, cells along the DV axis of the spinal cord of uninfected, MNR2-infected, and MNR2/Isl1-coinfected embryos, analyzed at stage 20. Diagram in FIG. 6O shows the DV divisions (bins A–F) of the spinal cord used to compile histograms shown in FIGS. 6P-1 through 6P-9. Bins B and C normally contain Isl1$^+$ D2 neurons and bin F contains V2 neurons. Values indicate number of ectopic cells, mean±SEM>300 cells in 30 sections for each marker.

FIG. 7.

Cooperation of Lim3 and Isl1 as Mediators of MNR2 Activity and Mimicry by HB9.

FIG. 7A.

Ectopic expression of Lim3 in the spinal cord of a Lim3-infected embryo, analyzed at stage 23.

FIG. 7B.

Absence of ectopic MNR2$^+$ cells in the spinal cord of a Lim3-infected embryo. Analysis of more than 4000 ectopic Lim3$^+$ cells.

FIG. 7C.

Absence of ectopic Isl2$^+$ cells in the spinal cord of a Lim3-infected embryo. Analysis of more than 5000 ectopic Lim3$^+$ cells.

FIG. 7D.

Low incidence of ectopic expression of HB9 in the spinal cord of a Lim3-infected embryo. All ectopic HB9 cells coexpress Isl1. Analysis of more than 5000 ectopic Lim3$^+$ cells.

FIG. 7E.

Quantitation of ectopic Isl1$^+$, Isl2$^+$ and HB9$^+$ cells in the dorsal spinal cord of a Lim3-infected embryo. Analysis of 300–600 Lim3$^+$ cells.

FIG. 7F.

Ectopic expression of Chx10 in the spinal cord of a Lim3-infected embryo. All ectopic Chx10⁺ cells coexpress Lim3.

FIG. 7G.

Same image as in FIG. 7F, showing that ectopic Chx10⁺ cells are located both dorsal and ventral (arrowheads) to the position of Isl⁺ motor neurons.

FIG. 7H.

Coexpression of Isl1 and Lim3 in the spinal cord of a Lim3/Isl1 coinfected embryo.

FIG. 7I.

Isl2 expression is not detected in the spinal cord of a Lim3/Isl1 coinfected embryo.

FIG. 7J.

A high incidence of ectopic HB9 expression is detected in the spinal cord of a Lim3/Isl1 coinfected embryo.

FIG. 7K.

Ectopic Isl12 and HB9 expression in the dorsal spinal cord of Lim3/Isl1 infected embryos. Analysis of 300–600 neurons from six infected embryos.

FIG. 7L.

Expression of HB9 in the spinal cord of an HB9-infected embryo analyzed at stage 23.

FIG. 7M.

Ectopic dorsal expression of Isl2 in the spinal cord of an HB9-infected embryo. Analysis from >10 infected embryos.

FIG. 7N.

Ectopic dorsal expression of Lim3 in the spinal cord of an HB9-infected embryo.

FIG. 8.

Role of MNR2 in the Shh-Induced Pathway of Somatic Motor Neuron and V2 Interneuron Generation. In this model, homeodomain proteins (MNR2, Isl2, HB9) are restricted to the somatic motor neuron lineage and Lim 3, Chx10, V2 Interneuron to the V2 interneuron lineage. Vertical gray bar indicates time of exit from the cell cycle. The diagram indicates the subordinate activities of Lim3 and Isl1 in the activation of HB9, the requirement for Isl1 in the induction of HB9 and Isl2, and the autoactivation of MNR2. In the absence of MNR2 activity, Lim3 is sufficient to induce Chx10. For details see the text.

FIG. 9

Suppression of Spinal Interneuron Fates by MNR2.

FIG. 9A.

Schematic diagram of the position of D1 (LH2⁺), D2 (Isl1⁺), V1 (En1⁺) and V2 (Chx10⁺) interneurons in the spinal cord of a stage 20–22 chick embryo.

FIG. 9B.

Section through the spinal cord of a stage 22 MNR2-infected embryo showing the asymmetric distribution of ectopic MNR2⁺ cells, which are restricted almost exclusively to the right half of the spinal cord of this embryo.

FIGS. 9C–N.

Figures 9I, 9J, 9K:
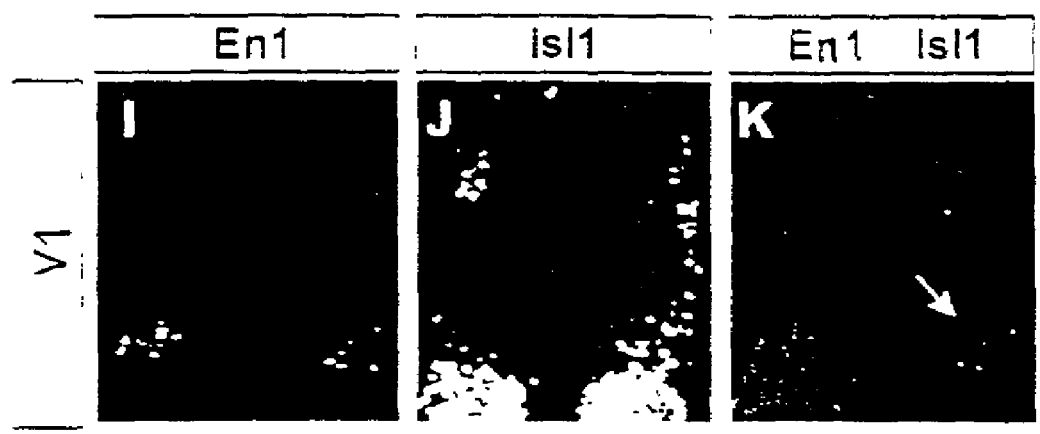
Figures 9L, 9M, 9N:
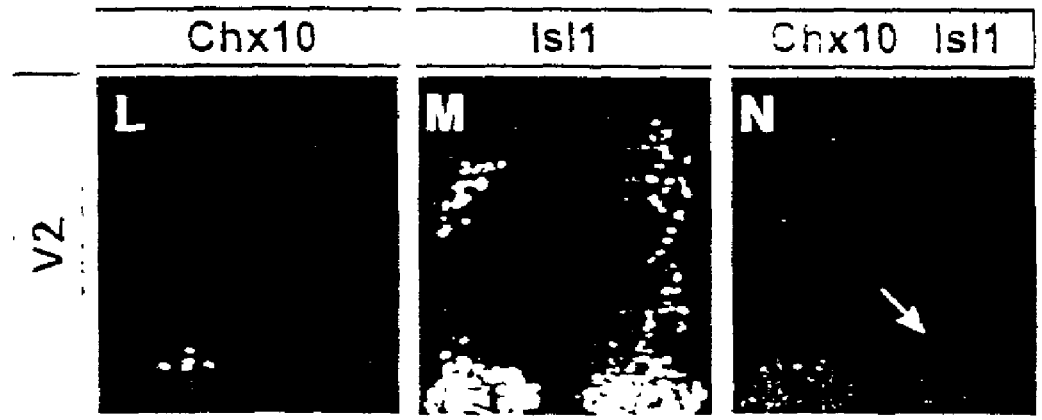

Sections through the same embryo shown in FIG. 9B. double or triple-labeled to reveal ectopic Isl1⁺ neurons and the expression of D1, D2, V1 and V2 interneuron markers.

FIGS. 9C–E.

Shows the reduction (approximately 75%) in LH2 expression in the right half of the infected embryo.

FIGS. 9F–H.

Shows the reduction in Brn 3.0 expression (88±4%, n=4 sections) in the right half of the infected spinal cord.

FIGS. 9I–K.

Shows the reduction in En1 expression (46±5%; n=10 sections) in the right half of the infected spinal cord.

FIGS. 9L–N.

Shows the reduction in Chx10 expression (89±3%; n=9 sections) in the right half of the infected spinal cord. A similar repression of interneuron marker expression was detected in six other MNR2-infected embryos.

FIG. 10 cMNR2 Protein and the Predicted Amino Acid Sequence (SEQ ID NO: 1).

FIG. 11 cMNR2 DNA Nucleotides 1–1736. (SEQ ID NO: 2).

FIG. 12 cHB9 Protein and the Predicted Amino Acid Sequence (SEQ ID NO: 3).

FIG. 13 cHB9 DNA Nucleotides 1–1534. (SEQ ID NO: 4).

DETAILED DESCRIPTION OF THE INVENTION

The following standard abbreviations are used throughout the specification to indicate specific nucleotides:
C=cytosine
A=adenosine
T=thymidine
G=guanosine This invention provides an isolated nucleic molecule encoding a motor neuron restricted pattern, MNR2, protein. In an embodiment the isolated nucleic molecule encoding a motor neuron restricted pattern, MNR2, protein is a DNA molecule. In another embodiment the isolated nucleic acid molecule encoding a motor neuron restricted pattern, MNR2, protein is a cDNA molecule. In a further embodiment the isolated DNA molecule encoding a motor neuron restricted pattern, MNR2, protein is a RNA molecule. In an embodiment the isolated nucleic acid molecule encoding a motor neuron restricted pattern is operatively linked to a promoter of RNA transcription.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide, MNR2, and as products for the large scale synthesis of the polypeptide MNR2, or fragments thereof, by a variety of recombinant techniques. The DNA molecule is useful for generating new cloning and expression vectors, transformed and transfected prokaryotic and eukaryotic host cells, and new and useful methods for cultured growth of such host cells capable of expression of the polypeptide MNR2 or portions thereof and related products.

In another embodiment the isolated nucleic acid molecule which is a cDNA molecule which, encoding a motor neuron restricted pattern MNR2 protein, encodes a chick MNR2 protein. In another embodiment the isolated nucleic acid molecule is a cDNA molecule wherein the nucleic acid molecule encodes a chick MNR2 protein comprising the amino acid sequence set forth in SEQ ID NO: 1. In a further embodiment the isolated nucleic acid molecule is a cDNA molecule wherein the nucleic acid molecule encodes a mammalian MNR2 protein. In an embodiment the isolated nucleic acid molecule is a cDNA molecule wherein the nucleic acid molecule encodes a mammalian MNR2 protein which is a mouse, rat or human protein. In an embodiment the isolated nucleic acid molecule is a cDNA molecule, which comprises the nucleic acid sequence set forth in SEQ ID NO: 2.

This invention provides a vector which comprises the isolated nucleic acid encoding a motor neuron restricted pattern, MNR2, protein operatively linked to a promoter of RNA transcription. In an embodiment a plasmid comprises the vector which comprises the isolated nucleic acid encoding a motor neuron restricted pattern, MNR2, protein. In another embodiment the plasmid comprises a vector which comprises the isolated nucleic acid encoding a chick motor neuron restricted pattern, pMNR2, protein.

In an embodiment, a full-length cDNA nucleic acid molecule encoding a MNR2 protein is inserted into a pcs2$^+$ plasmid and the resulting plasmid is designated as pcs2$^+$ cMNR2.3. The plasmid is with ampicillin resistance and 1.2 kilobase insert is releasable by cleavage with ClaI restriction endonuclease. Plasmid pcs2$^+$cMNR2.3 was deposited on Sep. 28, 1998 with the American Type Culture Collection (ATCC), 10801 University Boulevard, Manassas, Va. 20110-2209, U.S.A. under the provisions of the Budapest Treaty for the International Recognition of the Deposit of Microorganisms for the Purposes of Patent Procedure. Plasmid pcs2$^+$cMNR2.3 was accorded ATCC Accession Number 203294.

Numerous vectors for expressing the inventive proteins may be employed. Such vectors, including plasmid vectors, cosmid vectors, bacteriophage vectors and other viruses, are well known in the art. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus. Additionally, cells which have stably integrated the DNA into their chromosomes may be selected by introducing one or more markers which allow for the selection of transfected host cells. The markers may provide, for example, prototrophy to an auxotrophic host, biocide resistance or resistance to heavy metals such as copper. The selectable marker gene can be either directly linked to the DNA sequences to be expressed, or introduced into the same cell by cotransformation.

Regulatory elements required for expression include promoter sequences to bind RNA polymerase and transcription initiation sequences for ribosome binding. Additional elements may also be needed for optimal synthesis of mRNA. These additional elements may include splice signals, as well as enhancers and termination signals. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well known in the art, for example the methods described above for constructing vectors in general.

These vectors may be introduced into a suitable host cell to form a host vector system for producing the inventive proteins. Methods of making host vector systems are well known to those skilled in the art.

Methods of introducing nucleic acid molecules into cells are well known to those of skill in the art. Such methods include, for example, the use of viral vectors and calcium phosphate co-precipitation.

The "suitable host cell" in which the nucleic acid molecule encoding is MNR2 protein capable of being expressed is any cell capable of taking up the nucleic acid molecule and stably expressing the MNR2 encoded thereby.

This invention provides a host cell containing the vector which comprises the isolated nucleic acid encoding a motor neuron restricted pattern, MNR2, protein. In an embodiment the host cell is selected from a group consisting of a bacterial cell, a plant cell, an insect cell and a mammalian cell.

Suitable host cells include, but are not limited to, bacterial cells (including gram positive cells), yeast cells, fungal cells, insect cells and animal cells. Suitable animal cells include, but are not limited to HeLa cells, Cos cells, CV1 cells and various primary mammalian cells. Numerous mammalian cells may be used as hosts, including, but not limited to, the mouse fibroblast cell NIH-3T3 cells, CHO cells, HeLa cells, Ltk$^-$ cells and COS cells. Mammalian cells may be transfected by methods well known in the art such as calcium phosphate precipitation, electroporation and microinjection.

This invention provides a method of producing a polypeptide having the biological activity of a mammalian MNR2 which comprises growing host cells selected from a group consisting of bacterial, plant, insect or mammalian cell, under suitable conditions permitting production of the polypeptide. In another embodiment of the method of producing a polypeptide having the biological activity of a mammalian MNR2 the method further comprises of the recovering the produced polypeptide.

This invention provides an isolated nucleic acid molecule of at least 15 contiguous nucleotides capable of specifically hybridizing with a unique sequence included within the sequence of the nucleic acid molecule encoding a motor neuron restricted pattern, MNR2, protein. In an embodiment the isolated nucleic acid molecule of at least 15 contiguous nucleotides capable of specifically hybridizing with a unique sequence included within the sequence of the nucleic acid molecule encoding a motor neuron restricted pattern, MNR2, protein is a DNA molecule. In another embodiment the isolated nucleic acid molecule of at least 15 contiguous nucleotides capable of specifically hybridizing with a unique sequence included within the sequence of the nucleic acid molecule encoding a motor neuron restricted pattern, MNR2, protein, is a RNA molecule.

This invention provides an isolated nucleic acid molecule capable of specifically hybridizing with a unique sequence included within the sequence of a nucleic acid molecule which is complementary to the nucleic acid molecule encoding a motor neuron restricted pattern, MNR2, protein. In an embodiment the isolated nucleic acid molecule capable of specifically hybridizing with a unique sequence included within the sequence of a nucleic acid molecule which is complementary to the nucleic acid molecule encoding a motor neuron restricted pattern, MNR2, protein, is a DNA molecule. In another embodiment the isolated nucleic acid molecule capable of specifically hybridizing with a unique sequence included within the sequence of a nucleic acid molecule which is complementary to the nucleic acid molecule encoding a motor neuron restricted pattern, MNR2, protein is a RNA molecule.

One of ordinary skill in the art will easily obtain unique sequences from the cDNA cloned in the pcs2$^{30}$ cMNR2.3 plasmid. Such unique sequences may be used as probes to screen various mammalian cDNA libraries and genomic DNAs, e.g. mouse, rat and bovine, to obtain homologous nucleic acid sequences and to screen different cDNA tissue libraries to obtain isoforms of the obtained nucleic acid sequences. Nucleic acid probes from the cDNA cloned in the pcs2$^+$cMNR2.3 plasmid may further be used to screen other human tissue cDNA libraries to obtain isoforms of the nucleic acid sequences encoding MNR2 protein as well as to screen human genomic DNA to obtain the analogous nucleic acid sequences. The homologous nucleic acid sequences and isoforms may be used to produce the proteins encoded thereby.

As used herein, "capable of specifically hybridizing" means capable of binding to an mRNA molecule encoding a MNR2 but not capable of binding to an mRNA molecule encoding a MNR2 receptor protein.

This invention provides an antisense oligonucleotide having a nucleic acid sequence capable of specifically hybridizing to an mRNA molecule encoding a MNR2 protein. In an embodiment the antisense oligonucleotide has a nucleic acid sequence capable of specifically hybridizing to the isolated cDNA molecule encoding a motor neuron restricted pattern, MNR2, protein. In an embodiment the antisense oligonucleotide has a nucleic acid sequence capable of specifically hybridizing to an isolated RNA molecule encoding a motor neuron restricted pattern, MNR2 protein.

This invention provides a purified MNR2 protein. In an embodiment the purified MNR2 protein is encoded by an isolated nucleic acid encoding a motor neuron restricted pattern, MNR2, protein. In another embodiment the MNR2 protein unique polypeptide fragment of the purified MNR2 protein. In an embodiment the purified MNR2 protein has substantially the same amino acid sequence as set forth in SEQ ID NO: 1. In a further embodiment the purified MNR2 protein having an amino acid sequence as set forth in SEQ ID NO: 1. In another embodiment the purified MNR2 protein has an amino acid sequence as set forth in SEQ ID NO: 1. In a further embodiment, the MNR2 protein is a vertebrate MNR2 protein. In an embodiment the purified vertebrate MNR2 protein having an amino acid sequence as set forth in SEQ ID NO: 12 is a chick, mouse or rat MNR2 protein.

As used herein, an MNR2 protein having "substantially the same" amino acid sequences as set forth in SEQ ID NO: 1 is encoded by a nucleic acid encoding MNR2, said nucleic acid having 100% identity in the homeodomain regions, that is those regions coding the protein, and said nucleic acid may vary in the nucleotides in the non-coding regions.

This invention provides a monoclonal antibody directed to an epitope of an MNR2 protein. In an embodiment the monoclonal antibody is directed to a chick, mouse or rat MNR2 protein.

This invention provides a polyclonal antibody directed to an epitope of the purified MNR2 protein having the amino sequence as set forth in SEQ ID No: 1. In a further embodiment the monoclonal or polyclonal antibodies are directed to the MNR2 protein, having the amino sequence as set forth in SEQ ID NO: 1.

Polyclonal antibodies may be produced by injecting a host animal such as rabbit, rat, goat, mouse or other animal with the immunogen of this invention, e.g. a purified mammalian MNR2 protein or a purified human MNR2 protein. The sera are extracted from the host animal and are screened to obtain polyclonal antibodies which are specific to the immunogen. Methods of screening for polyclonal antibodies are well known to those of ordinary skill in the art such as those disclosed in Harlow & Lane, *Antibodies: A Laboratory Manual,* (Cold Spring Harbor Laboratories, Cold Spring Harbor, N.Y.: 1988) the contents of which are hereby incorporated by reference.

The monoclonal antibodies may be produced by immunizing for example, mice with an immunogen. The mice are inoculated intraperitoneally with an immunogenic amount of the above-described immunogen and then boosted with similar amounts of the immunogen. Spleens are collected from the immunized mice a few days after the final boost and a cell suspension is prepared from the spleens for use in the fusion.

Hybridomas may be prepared from the splenocytes and a murine tumor partner using the general somatic cell hybridization technique of Kohler, B. and Milstein, C., Nature (1975) 256: 495–497. Available murine myeloma lines, such as those from the American Type Culture Collection (ATCC) 12301 Parklawn Drive, Rockville, Md. 20852 USA, may be used in the hybridization. Basically, the technique involves fusing the tumor cells and splenocytes using a fusogen such as polyethylene glycol. After the fusion the cells are separated from the fusion medium and grown in a selective growth medium, such as HAT medium, to eliminate unhybridized parent cells. The hybridomas may be expanded, if desired, and supernatants may be assayed by conventional immunoassay procedures, for example radioimmunoassay, using the immunizing agent as antigen. Positive clones may be characterized further to determine whether they meet the criteria of the invention antibodies.

Hybridomas that produce such antibodies may be grown in vitro or in vivo using known procedures. The monoclonal antibodies may be isolated from the culture media or body fluids, as the case may be, by conventional immunoglobulin purification procedures such as ammonium sulfate precipitation, gel electrophoresis, dialysis, chromatography, and ultrafiltration, if desired.

In the practice of the subject invention any of the above-described antibodies may be labeled with a detectable marker. In one embodiment, the labeled antibody is a purified labeled antibody. As used in the subject invention, the term "antibody" includes, but is not limited to, both naturally occurring and non-naturally occurring antibodies. Specifically, the term "antibody" includes polyclonal and monoclonal antibodies, and binding fragments thereof. Furthermore, the term "antibody" includes chimeric antibodies and wholly synthetic antibodies, and fragments thereof.

Furthermore, the term "antibody" includes chimeric antibodies and wholly synthetic antibodies, and fragments thereof. A "detectable moiety" which functions as detectable labels are well known to those of ordinary skill in the art and include, but are not limited to, a fluorescent label, a radioactive atom, a paramagnetic ion, biotin, a chemiluminescent label or a label which may be detected through a secondary enzymatic or binding step. The secondary enzymatic or binding step may comprise the use of digoxigenin, alkaline phosphatase, horseradish peroxidase, β-galactosidase, fluorescein or steptavidin/biotin. Methods of labeling antibodies are well known in the art.

Determining whether the antibody forms such a complex may be accomplished according to methods well known to those skilled in the art. In the preferred embodiment, the determining is accomplished according to flow cytometry methods.

The antibody may be bound to an insoluble matrix such as that used in affinity chromatography. As used in the subject invention, isolating the cells which form a complex with the immobilized monoclonal antibody may be achieved by standard methods well known to those skilled in the art. For example, isolating may comprise affinity chromatography using immobilized antibody.

Alternatively, the antibody may be a free antibody. In this case, isolating may comprise cell sorting using free, labeled primary or secondary antibodies. Such cell sorting methods are standard and are well known to those skilled in the art.

The labeled antibody may be a polyclonal or monoclonal antibody. In one embodiment, the labeled antibody is a purified labeled antibody. The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof. The detectable marker may be, for example, radioactive or fluorescent. Methods of labeling antibodies are well known in the art.

This invention provides a method of inducing differentiation of somatic motor neurons which comprises expressing MNR2 protein in any neural progenitor cells. In an embodiment of the method, expression of MNR2 protein induces expression of transcription factors Isl2, Lim 3 and HB9. In a further embodiment of the method of inducing differentiation of somatic motor neurons the neural progenitor cells are spinal cord or hindbrain motor neuron progenitor cells.

This invention provides a transgenic nonhuman mammal which comprises an isolated nucleic acid, including a motor neuron restriction pattern, MNR2 protein, which is a DNA molecule. In an embodiment of the transgenic nonhuman mammal the DNA encoding a MNR2 protein is operatively linked to tissue specific regulatory elements.

This invention provides a method of determining physiological effects of expressing varying levels of MNR2 protein in a transgenic nonhuman mammal which comprises producing a panel of transgenic nonhuman animals, each nonhuman mammal expressing a different amount of MNR2 protein.

This invention provides a method of producing isolated purified MNR2 protein which comprises: a) inserting a nucleic acid molecule encoding an MNR2 protein into a suitable vector; b) introducing the resulting vector into a suitable host cell; c) selecting the introduced host cell for the expression of the MNR2 protein; d) culturing the selected cell to produce the MNR2 protein; and e) recovering the MNR2 protein produced.

This invention provides a method of inducing differentiation of somatic motor neurons in a subject comprising administering to the subject the purified MNR2 protein in an amount effective to induce differentiation of somatic motor neurons in the subject. In an embodiment, a functionally equivalent analog of MNR2 is administered to the subject. In an embodiment of the method of inducing differentiation of somatic motor neurons in a subject comprising administering to the subject the purified MNR2 protein in an amount effective to induce differentiation of somatic motor neurons in the subject, the subject is a mammal. In another embodiment of the above-described method of inducing differentiation of somatic motor neurons in a subject, the subject is a chick, mouse, rat or human.

As used herein, "subject" means any animal or artificially modified animal. Artificially modified animals include, but are not limited to, SCID mice with human immune systems. In the preferred embodiment, the subject is a human.

This invention provides a pharmaceutical composition comprising a purified MNR2 protein and a pharmaceutically acceptable carrier.

The invention also provides a pharmaceutical composition comprising a effective amount of the MNR2 proteins described above and a pharmaceutically acceptable carrier. In the subject invention an "effective amount" is any amount of above-described MNR2 proteins which, when administered to a subject suffering from a disease or abnormality against which the proteins are determined to be potentially therapeutic, are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The above described pharmaceutical composition comprising MNR2 protein can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The above described pharmaceutical composition comprising MNR2 protein can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular above described pharmaceutical composition comprising MNR2 protein in use, the strength of the preparation, the mode of administration, and the advancement of the disease condition or abnormality. Additional factors depending on the particular subject being treated will result in a need to adjust dosages, including subject age, weight, gender, diet, and time of administration.

The subject invention further provides a composition which comprises an effective amount of a nucleic acid molecule encoding MNR2 capable of being expressed in a suitable host cell, and a pharmaceutically acceptable carrier.

This invention provides a method for treating a subject afflicted with an abnormality associated with a lack of one or more normally functioning motor neurons which comprises introducing an amount of the pharmaceutical composition comprising of a purified MNR2 protein and a pharmaceutically acceptable carrier effective to generate somatic motor neurons from undifferentiated motor neuron precursor cells in the subject, thereby treating the subject afflicted with the abnormality associated with the lack of one or more normally functioning motor neurons.

As used herein a "normally functioning motor neuron" is a motor neuron that can control muscle contraction and respond to sensory input.

As used herein, administering may be effected or performed using any of the various methods known to those skilled in the art. The administration may be intravenous, intraperitoneal, intrathecal, intralymphatical, intramuscular, intralesional, parenteral, epidural, subcutaneous; by infusion, liposome-mediated delivery, aerosol delivery; topical, oral, nasal, anal, ocular or otic delivery.

This invention provides a method of treating a subject afflicted with a neurodegenerative disease which comprises introducing an amount of the pharmaceutical composition which comprises a purified MNR2 protein and a pharmaceutically acceptable carrier effective to generate somatic motor neurons from undifferentiated precursor motor neuron cells in the subject, thereby treating the subject afflicted with the neurodegenerative disease. In an embodiment of the method of treating a subject with a neurodegenerative disease which comprises introducing an amount of pharmaceutical composition which comprises a purified MNR2 protein and a pharmaceutically acceptable carrier effective to generate somatic motor neurons from undifferentiated precursor motor neuron cells in the subject, the generation of motor neurons from undifferenitated precursor motor neuron cells alleviates a chronic neurodegenerative disease. In an embodiment of the above-described method of treating a subject afflicted with a chronic neurodegenerative disease where the disease is a spinal muscular atrophy. In a further embodiment the of method of treating a subject afflicted with a chronic neurodegenerative disease the disease is amyotrophic lateral sclerosis (Lou Gehrig's Disease).

This invention provides for a method of treating a subject afflicted with an acute nervous system injury which comprises introducing an amount of a pharmaceutical composition which comprises a purified MNR2 protein and a pharmaceutically acceptable carrier effective to generate motor neurons from undifferentiated precursor motor neuron cells in a subject, thereby treating the subject afflicted with the acute nervous system injury.

This invention provides for a method of treating a subject afflicted with an acute nervous system injury which comprises introducing an amount of pharmaceutical composition which comprises a purified MNR2 protein and a pharmaceutically acceptable carrier effective to generate motor neurons from undifferentiated precursor motor neuron cells in a subject, wherein the acute nervous system injury is localized to a specific central axon which comprises surgical implantation of the pharmaceutical compound comprising a MNR2 protein and a pharmaceutically acceptable carrier effective to generate motor neurons from undifferentiated precursor motor neuron cells located proximal to the specific central axon, so as to alleviate the acute nervous system injury localized to a specific central axon, thereby treating the subject afflicted with the acute nervous system injury.

This invention provides a method for diagnosing a chronic neurodegnerative disease associated with the expression of a MNR2 protein in a sample from a subject which comprises: a. obtaining DNA from the sample of the subject suffering from the chronic neurodegenerative disease; b. performing a restriction digest of the DNA with a panel of restriction enzymes; c. separating the resulting DNA fragments by size fractionation; d. contacting the resulting DNA fragments with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; e. detecting labeled bands which have hybridized to the nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence to create a unique band pattern specific to the DNA of subjects suffering from the chronic neurodegenerative disease; f. preparing DNA obtained from a sample of a subject for diagnosis by steps (a–e); and g. comparing the detected band pattern specific to the DNA obtained from a sample of subjects suffering from the chronic neurodegenerative disease from step (e) and the DNA obtained from a sample of the subject for diagnosis from step (f) to determine whether the patterns are the same or different and to diagnose thereby predisposition to the chronic neurodegenerative disease if the patterns are the same.

This invention provides a method for diagnosing a chronic neurodegenerative disease associated with the expression of a MNR2 protein in a sample from a subject which comprises: a. obtaining RNA from the sample of the subject suffering from chronic neurodegenerative disease; b. separating the RNA sample by size fractionation; c. contacting the resulting RNA species with a nucleic acid probe capable of specifically hybridizing with a unique sequence included within the sequence of a nucleic acid molecule encoding a MNR2 protein, wherein the sequence of a nucleic acid molecule encoding a MNR2 protein is linked at a specific break point to a specified nucleic acid sequence and labeled with a detectable marker; d. detecting labeled bands which have hybridized to the RNA species to create a unique band pattern specific to the RNA of subjects suffering from the chronic neurodegenerative disease; f. preparing RNA obtained from a sample of a subject for diagnosis by steps (a–d); and g. comparing the detected band pattern specific to the RNA obtained from a sample of subjects suffering from the chronic neurodegenerative disease from step (d) and the RNA obtained from a sample of the subject for diagnosis from step (f) to determine whether the patterns are the same or different and to diagnose thereby predisposition to the chronic neurodegenerative disease if the patterns are the same.

This invention provides a functionally equivalent analog of MNR2 that induces MNR2 differentiation of neural progenitor cells.

This invention provides a functionally equivalent analog of MNR2 that prevents MNR2 differentiation of neural progenitor cells.

This invention provides a method of treating a subject afflicted with a neuromuscular disease which comprises introducing an amount of a pharmaceutical composition comprising a purified MNR2 protein and a pharmaceutically acceptable carrier effective to activate acetylcholine to activate muscle cells.

In order to facilitate an understanding of the Experimental Details section which follows, certain frequently occurring methods and/or terms are best described in Sambrook, et al. (1989).

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Single-Cell Library Screen

Culture of stage 10 chick (Hamburger and Hamilton, 1951) [i] explants was performed as described (Yamada et al.,1993). After 24 hr, explants were enzymatically dissociated and single cells isolated. The synthesis and amplification of cDNAs isolated from single cells was performed essentially as in Dulac and Axel (1995). Single cell-derived cDNAs were analyzed using Isl1, Isl2, HB9 and Lim2 probes. The efficiency of cDNA amplification was assessed using S17. A single cell cDNA sample that revealed Isl1, Isl2 and HB9 hybridization was used to prepare a cDNA library in λZapII (Stratagene). Approximately 2000 plaques were screened with cDNAs from a motor neuron and Lim2$^+$ neuron. Plaques hybridizing selectively with the motor neuron probe were isolated, cloned and analyzed by in situ hybridization. This screen generated 2 clones that encoded MNR2.

As used herein, "[i] explants" are intermediate neural plate explants.

Isolation of MNR2 and HB9

A single motor neuron-derived MNR2 cDNA clone was used to isolate a longer MNR2 cDNA. A genomic MNR2 clone containing the 5' coding region of MNR2 was ligated to the MNR2 cDNA to generate full-length chick MNR2. A chick HB9 cDNA was isolated from a spinal cord cDNA library using a PCR probe derived from the HB9 homeobox. A full length chick HB9 clone was constructed by ligating genomic HB9 coding sequence to the HB9 cDNA. Genbank accession numbers; chick MNR2 AF066860, chick HB9 AF066861.

Recombinant Retroviral Vectors

As used herein, a recombinant nucleic acid molecule is a nucleic acid molecule which does not occur as an individual molecule in nature and which is obtained through the use of recombinant technology.

Retroviral vectors were generated by subcloning chick cDNAs into either RCASBP(A) or RCASBP(B) vectors (Hughes et al., 1987; Morgan and Fekete, 1996). The RCAS(B) MNR2 3'Δ construct contained the coding region of MNR2 but lacked the 3' non-coding region. Viral supernatants (Morgan and Fekete, 1996) were applied to stage 5–6 chick embryos in ovo. In double infections, viral stocks derived from vectors encoding A or B envelope glycoproteins were mixed prior to in ovo application. Embryos were analyzed at stages 17–27.

Immunocytochemistry and In Situ Hybridization Histochemistry

Rabbit antisera were generated against a GST-chick MNR2 NH$_2$ fusion protein and against a KLH-conjugated chick HB9 NH$_2$ peptide (MEKSKNFRIDALLA) (SEQ ID NO.: 5). Mouse antisera and monoclonal antibodies were also generated against MNR2 protein and HB9 protein. Rabbit anti-Brn3.0 (Fedtsova and Turner, 1997); guinea pig anti Isl1/2 (Morton and T. M. Jessell unpublished data). For other antibody reagents see Ericson et al., (1997) and Liem et al., (1997). Immunohistochemistry was performed as described (Yamada et al., 1993). Double and triple-label analyses were performed with a Bio-Rad 1024 Confocal Microscope using Cy3, Cy5 and FITC-conjugated secondary antibodies (Jackson, Inc.). In situ hybridization was performed as described (Schaeren-Wiemers and Gerfin-Moser, 1993; Tsuchida et al., 1994) using MNR2 and ChAT (Yamada, et al., 1993) probes. The 3' non-coding MNR2 probe was the 300 bp SmaI-EcoRI fragment.

BrdU Incorporation into Neural Neurons

BrdU incorporation was analyzed after application of 100 uM BrdU to stage 18 embryos in ovo and subsequent incubation at 37° C. for 30 or 45 minutes.

Retrograde Labeling of Spinal Cord Cells

RCAS(B)MNR2-infected stage 24–26 embryos were dissected, ventral roots exposed and labeled by application of FITC-Dextran (Molecular Probes) (Varela-Echavarria et al., 1996). Embryos were incubated for 1 hour before analysis.

Materials and Methods

Isolation of MNR2

To identify genes expressed by somatic motor neuron progenitors, we performed a PCR-based differential screen (Dulac and Axel, 1995) of individual newly-differentiated motor neurons on the premise that genes expressed by motor neuron progenitors might persist transiently in post-mitotic motor neurons. Chick neural plate ([i]) explants (Yamada et al, 1993) were grown in vitro for 24 h, alone or with a concentration of Shh that induces somatic motor neurons (Ericson et al. 1997). cDNAs isolated from single cells derived from [i] explants exposed to Shh were hybridized with probes for three homeobox genes Isl1, Isl2 and HB9, that define post-mitotic somatic motor neurons (FIG. 1A). Single cell cDNA samples derived from [i] explants grown alone were hybridized with Lim2, a homeobox gene marker of spinal interneurons (FIG. 1A). A cDNA population amplified from a single Isl1$^+$, Isl2$^+$, HB9$^+$ motor neuron (FIG. 1A) was used to prepare a cDNA library that was screened with probes derived from a single in vitro generated motor neuron or Lim2$^+$ neuron. cDNAs isolated from plaques that hybridized selectively with the motor neuron-derived probe were cloned and sequenced. As used herein, "[i] explants" are intermediate neural plate explants.

Several genes identified in this manner were expressed in a motor neuron restricted pattern and we describe here the function of one of these, MNR2. MNR2 is a homeobox gene that encodes a homeodomain almost identical to that encoded by HB9 (FIG. 1B; Harrison et al., 1994), a gene whose neural expression is restricted to motor neurons (see below, Pfaff et al. 1996, Saha et al., 1997). The MNR2 sequence diverges from HB9 outside the homeodomain (FIG 1B; data not shown).

MNR2 is Expressed by Somatic Motor Neuron Progenitors

The pattern of neural expression of MNR2 was examined in chick embryos from stages 10 to 25. MNR2 expression was first detected at stage 12 in cells near the floor plate (FIG. 1C). At this stage, no motor neurons have been generated (Langman et al., 1966) and Isl1 is not yet expressed (Ericson et al., 1992). The onset of MNR2 expression coincides with the time that motor neuron progenitors acquire independence from Shh signaling (Ericson et al., 1996). Between stages 15–20, MNR2 expression was restricted to cells in the ventral spinal cord and caudal hindbrain, some of which were located medially and others laterally in a domain that overlaps with post-mitotic Isl1$^+$ motor neurons (FIG. 1D, 1E; data not shown).

We next examined whether, as predicted by the design of the differential screen, MNR2 is induced by Shh. To test this, [i] explants were exposed to Shh and the expression of MNR2 and Isl1/2 determined. Induction of MNR2 was detected 16 h after exposure to Shh (data not shown) and by 24 h, 70±12 (mean±SEM; n=4) MNR2$^+$ cells were detected (FIG. 1F, 1G). In addition, 32% of the induced MNR2$^+$ cells did not express Isl1/2 (FIG. 1G, 1H), consistent with the earlier onset of MNR2 expression in vivo. These results show that Shh induces MNR2.

To provide direct evidence that MNR2 is expressed by mitotic cells, we exposed stage 18 embryos to BrdU for 30 min and monitored the expression of MNR2 and Isl1 by BrdU$^+$ cells. Many MNR2$^+$, BrdU$^+$ cells (FIG. 2A) but no Isl1$^+$, BrdU$^+$ cells (FIG. 2B) were detected. In addition, a subset of MNR2$^+$ progenitors coexpressed the M-phase marker MPM2 (FIG. 2C; Westendorf et al., 1994). MNR2$^+$ progenitors coexpressed Pax6 (FIG. 2D; data not shown) but were located dorsal to the Nkx2.2$^+$ progenitor domain (FIG. 2E), supporting the idea that MNR2 expression is restricted to the progenitors of somatic motor neurons. MNR2 was also detected in post-mitotic somatic motor neurons in the spinal cord and hindbrain but not in visceral motor neurons (FIG. 1E , FIG. 2F and data not shown). Thus, MNR2 expression is restricted to domains of somatic motor neuron generation.

The temporal profile of MNR2 expression was compared with that of other homeodomain proteins that define somatic motor neurons. At spinal cord levels, the initial migration of newly-generated motor neurons occurs in a mediolateral plane (Leber and Sanes, 1995) and thus the more lateral the position of a motor neuron, the more advanced is its state of differentiation. Between stages 15 and 20, MNR2 was detected medially in progenitor cells as well as laterally in post-mitotic motor neurons (FIG. 2G-K, data not shown). The expression of Isl1 was restricted to post-mitotic motor neurons (FIG. 2G, 2K; Ericson et al., 1992) but appeared prior to HB9 and Isl2 (FIG. 2H, 2I, 2K; data not shown). In these laterally positioned motor neurons MNR2 expression was markedly decreased or absent (FIG. 2H, 2I, 2K) indicating that MNR2 expression is transient. Lim3 is expressed by post-mitotic somatic motor neurons (FIG. 2J, 2K; Tsuchida et al., 1994) but is also detected in Pax6$^+$ ventral progenitors and in these cells appears soon after MNR2 (FIG. 2J, 2K; data not shown). Thus, somatic motor neuron progenitors coexpress Pax6, MNR2 and Lim3.

MNR2 Induces the Expression of Somatic Motor Neuron Transcription Factors

If MNR2 has a critical role in the Shh-induced pathway of motor neuron generation, we reasoned that its misexpression might be sufficient to promote motor neuron differentiation in neural cells that have not been exposed to adequate levels of Shh and perhaps even in dorsal progenitor cells that are exposed to antagonistic BMP signals. To test this idea we misexpressed MNR2 in the neural tube using a replication competent retroviral vector (Morgan and Fekete, 1996). Embryos were infected with MNR2 virus at stages 5–6, permitted to develop until stages 20–27 and the resulting pattern of motor neuron differentiation monitored by expression of Isl1, Isl2, HB9, and Lim3. The expression of Isl2 and HB9 is restricted to somatic motor neurons (Tsuchida et al. 1994; Pfaff et al. 1996; data not shown) whereas Lim3 is also expressed by ventral (V2) interneurons that are generated immediately dorsal to motor neurons (FIG. 2J, 2K; Ericson et al. 1997). Isl1 is also expressed by dorsal (D2) interneurons (FIG. 2G, 2K; Liem et al. 1997).

In MNR2-infected embryos examined at stage 23, ectopic MNR2$^+$ cells were detected in a mosaic pattern throughout the spinal cord (FIG. 3A; data not shown). In dorsal regions that contained a high density of MNR2$^+$ cells, many ectopic Isl1$^+$, Isl2$^+$, HB9$^+$ and Lim3$^+$ cells were detected (FIG. 3B-E). All ectopic Isl1$^+$, Lim3$^+$, Isl2$^+$ and HB9$^+$ cells coexpressed MNR2 (FIG. 3F; data not shown) indicating that MNR2 acts cell-autonomously to activate the expression of these homeodomain proteins. To control for the specificity of MNR2 activity, we misexpressed Lmx1b and Hoxc6, two other homeobox genes present in the spinal cord (Burke and Tabin 1996; Riddle et al. 1995). Neither Lmx1b nor Hoxc6 induced MNR2, Lim3, Isl1, Isl2 or HB9 (data not shown). Thus, the activity of MNR2 is not mimicked by divergent homeodomain proteins.

We next examined whether the ability of MNR2 to induce motor neuron markers in the dorsal spinal cord is associated with a change in the early dorsal character of neural progenitor cells. The ectopic dorsal expression of MNR2 did not repress Pax7 (FIG. 3G), a marker of dorsal progenitor cells (Ericson et al., 1996). The detection of Isl2+, HB9+ and Lim3+ cells in the extreme dorsal region of the spinal cord (FIG. 3C-E) also provides evidence that MNR2 can impose a somatic motor neuron character on neural cells that have been exposed to BMP signals (Liem et al., 1997). Consistent with this, there was no dorsoventral restriction in the positions at which cells expressing these ectopic homeodomain protein markers were found (FIG. 3B-E; data not shown). Ectopic expression of Lim3 and HB9 was also detected in dorsal root ganglion neurons (data not shown), indicating that MNR2 can also activate somatic motor neuron markers in peripheral neurons.

The ability of MNR2 to induce motor neuron transcription factors in the dorsal spinal cord leaves open the issue of whether ventral progenitor cells respond to MNR2 with the expression of motor neuron markers. The detection of a high incidence of MNR2-induced Isl1+, Isl2+ and HB9 cells below the Pax7 boundary (FIG. 3B-D, 3G) suggested that this is the case. Nevertheless, it remained possible that the ectopic location of these neurons arose through their dorsal migration from the normal domain of somatic motor neuron generation. We therefore examined whether MNR2 can induce motor neuron transcription factors in ventral progenitor cells generated in neural plate explants. Embryos were infected with MNR2 virus at stages 4–5 and permitted to develop until stage 10, at which time [i] explants were isolated and grown in vitro for 24 h with 0.5 nM Shh. This concentration of Shh is sufficient to repress Pax7 and generate a ventral progenitor cell state (Ericson et al., 1996), but is below the threshold for motor neuron induction (Ericson et al., 1997). [i] explants isolated from MNR2-infected embryos contained many MNR2+ cells and ~25 of these expressed Isl1/2 (FIG. 3H, 3I). In contrast, [i] explants derived from uninfected embryos and exposed to 0.5 nM Shh did not generate MNR2+ cells (FIG. 3J) or Isl1/2+ neurons (data not shown; Ericson et al., 1997). These results indicate that MNR2 can also direct motor neuron differentiation in ventral progenitor cells.

MNR2 Acts in the Context of a General Program of Neurogenesis

The expression of motor neuron transcription factors was detected in only a minority of ectopic MNR2+ cells (FIG. 3A-3F). In considering what might account for this restriction we noted that the ectopic expression of Isl1, Isl2 and HB9 coincided with the location of post-mitotic neurons (FIG. 3B-E). This observation, taken together with the normal restriction of Isl1, Isl2 and HB9 to post-mitotic motor neurons (FIG. 2K) raised the possibility that the induction of these homeodomain proteins by MNR2 might require cell cycle exit and the acquisition of a generic neuronal character.

To examine this possibility we first determined the proportion of ectopic MNR2+ cells that expressed Cyn1, a marker expressed by all spinal neurons soon after cell cycle exit (Ericson et al., 1997). At stages 20–23, only ~10% of ectopic MNR2+ cells expressed Cyn1 (FIG. 4A, 4B), indicating that most ectopic MNR2+ are progenitors. In contrast, >98% of MNR2-induced ectopic Isl1+, Isl2+ and HB9+ cells coexpressed Cyn1 (FIG. 4C-4E; data not shown). These findings suggest that the ectopic induction of Isl1, Isl2 and HB9 by MNR2 requires the acquisition of a post-mitotic neuronal character, thus conforming to the normal profile of expression of these three proteins in somatic motor neurons. Lim3, in contrast, is normally expressed by ventral progenitors as well as by post-mitotic motor neurons. Many MNR2-induced Lim3+ cells could be labeled after a brief BrdU pulse (FIG. 4F), ~70% of MNR2-induced ectopic Lim3+ cells coexpressed Cyn1 (data not shown) and only 55% of MNR2-induced Lim3+ cells coexpressed Isl1 (FIG. 4E, 4G). Thus MNR2 induces ectopic Lim3 expression in neural progenitors and post-mitotic neurons. These findings show that the normal temporal relationship between cell cycle exit and transcription factor expression is preserved in ectopic MNR2-induced neurons. In a neuronal context then, MNR2 is an efficient inducer of somatic motor neuron transcription factors: 91% of MNR2+ neurons expressed Isl1, 79% expressed Lim3 and ~40% expressed Isl2 and HB9 (FIG. 4H).

MNR2 Expression is Autoregulated

The onset of MNR2 expression occurs at the time that motor neuron progenitors attain independence from Shh signaling (Ericson et al., 1996). This finding raises the possibility that the progression of motor neuron progenitors to a Shh-independent state involves the expression of MNR2. One mechanism by which MNR2 might establish Shh-independence is through the activation of its own expression.

To test this, we infected embryos with a MNR2 3'Δ construct lacking 3' non-coding sequence and monitored the expression of endogenous MNR2 using a 3' non-coding probe. Retrovirally-introduced MNR2 3'Δ induced endogenous MNR2 in dorsal spinal cord cells (FIG. 4I, 4J). Moreover, the ectopic expression of MNR2 was not restricted to neural cells (FIG. 4J), in contrast to the neural restriction in the MNR2-induced ectopic expression of Lim3, Isl1, Isl2 and HB9 (FIG. 3; data not shown). These results support the idea that MNR2 expression and autoactivation underlies the progression of motor neuron progenitors to a Shh-independent state.

MNR2 Induces Later Features of Motor Neuron Differentiation

The sufficiency of MNR2 as an inducer of somatic motor neuron transcription factors prompted us to examine whether these neurons exhibit other aspects of the motor neuron phenotype. We first examined if MNR2 can induce the expression of ChAT: the gene encoding the rate limiting enzyme in the synthesis of acetylcholine, the motor neuron neurotransmitter. In control embryos, ChAT expression was restricted to the region occupied by motor neuron cell bodies and their dendrites (FIG. 5A, 5C, 5E). In contrast, in MNR2-infected embryos, ChAT was expressed ectopically by cells in the dorsal spinal cord (FIG. 5B, 5D, 5E). Thus, MNR2 induces the gene that defines the transmitter phenotype of motor neurons.

We next examined whether neurons in the dorsal spinal cord that express MNR2 acquire the motor neuron-specific feature of an axonal projection into the ventral root. To assess this we labeled spinal neurons retrogradely by application of FITC-Dextran to the ventral roots of stage 25 embryos. In control embryos, labeled neurons were restricted to the ventral spinal cord (FIG. 5F, 5J). In MNR2-infected embryos, many ectopic dorsal MNR2+, Isl1/2+ neurons were labeled with FITC-Dextran and these neurons projected axons towards the ventral root exit point (FIG. 5G-J). In addition, ectopic expression of SC1, a surface marker of motor neurons (Tanaka and Obata, 1984) was detected in MNR2-infected but not in control embryos (data not shown). These findings show that MNR2 induces later phenotypic features of somatic motor neurons.

Ectopic Expression of MNR2 Represses Interneuron Fates

The detection of ectopic motor neuron differentiation in dorsally-located neurons raised the question of whether the interneuronal character of spinal cord neurons is suppressed by MNR2. To address this issue we analyzed the expression of homeodomain proteins that define four classes of interneurons generated in domains dorsal to motor neurons. Dorsally, D1 neurons express LH2 (Liem et al., 1997) and many D2 neurons express Brn3.0 (Fedtsova and Turner, 1997). Ventrally, V1 neurons express En1 (Ericson et al., 1997) and Lim3$^+$ V2 neurons express Chx10 (Ericson et al. 1997).

In MNR2-infected embryos D1, D2, V1 or V2 interneuron markers were not detected in ectopic Isl2$^+$ and HB$^+$9 neurons (data not shown). In regions of the spinal cord in which a high proportion of cells in these interneuron domains ectopically expressed MNR2 there was a ~50–90% decrease in the number of cells that expressed D1, D2, V1 and V2 neuron markers (Table 1).

TABLE 1

Suppression of Spinal Interneuron Fates by MNR2

| Interneuron Population | Homeodomain Protein Marker | Reduction in Marker Expression |
|---|---|---|
| D1 | LH2 | 75% (1) |
| D2 | Brn3.0 | 88 ± 4% (4) |
| V1 | En1 | 46 ± 5% (10) |
| V2 | Chx10 | 89 ± 3% (9) |

Analysis derived from spinal cord of a stage 22 MNR2-infected embryo in which ectopic MNR2$^+$ cells were restricted almost exclusively to the right half of the spinal cord. Values (%) indicate number of labeled cells on heavily infected vs uninfected sides. Mean ± SEM, n = number of sections. A similar repression of interneuron markers was detected in six other MNR2-infected embryos.

The differing degrees of extinction of these interneuron markers appear to reflect local variation in the density of ectopic MNR2$^+$ cells rather than any difference in the efficiency with which MNR2 suppresses individual interneuron fates. The induction of somatic motor neuron differentiation by MNR2 is therefore accompanied by the suppression of interneuron fates.

Cooperation of Isl1 and MNR2 in the Specification of Somatic Motor Neuron Identity We next addressed the contributions of the transcription factors induced by MNR2 to the differentiation of somatic motor neurons. To examine the role of Isl1 in the program of somatic motor neuron differentiation we assayed motor neuron markers in embryos infected with Isl1 virus. No ectopic expression of MNR2, Lim3, Isl2 or HB9 was detected (FIG. 6A-6E). Thus, Isl1 is not sufficient to direct somatic motor neuron differentiation. Nevertheless, all MNR2-induced ectopic dorsal Isl2$^+$ and HB9$^+$ neurons coexpressed Isl1 (FIG. 4E). This observation, together with the requirement for Isl1 in the generation of somatic motor neurons (Pfaff et al., 1996) suggested that the ectopic expression of Isl2 and HB9 induced by MNR2 involves Isl1.

To test this we analyzed the activity of MNR2 at an earlier stage of development (stage 20). We reasoned that if Isl1 cooperates with MNR2 in the induction of Isl2 and HB9, then the early onset of Isl1 expression by prospective D2 neurons (Liem et al., 1997) might relieve the delay inherent in the induction of Isl1 by MNR2 and thus accelerate MNR2-induced motor neuron differentiation. MNR2 induced ectopic dorsal expression of Isl2 and HB9 at stage 20 (FIG. 6F-6J). However there was a restriction in the position of ectopic Isl2$^+$ and HB9$^+$ cells, focused on the normal domain of D2 neuron generation (FIG. 6F-6J, 6P). If this restriction is conferred by the early expression of Isl1 by prospective D2 neurons then coinfection with MNR2 and Isl1 viruses would be expected to abolish the dorsoventral restriction in Isl2 and HB9 expression. In the spinal cord of embryos coinfected with MNR2 and Isl1 viruses and analyzed at stage 20, a high proportion of cells now coexpressed MNR2 and Isl1 at ectopic locations (FIG. 6K). Over 70% of these cells coexpressed Isl2 and/or HB9 (FIG. 6N). Moreover, the dorsoventral restriction in the position of ectopic Isl2$^+$ and HB9$^+$ neurons evident after MNR2 infection was abolished (FIGS. 6L, 6M, 6P). These findings support the idea that the induction of Isl2 and HB9 by MNR2 involves the cooperation of Isl1.

MNR2 Acts Upstream of Lim3 in the Specification of Somatic Motor Neurons

During normal somatic motor neuron differentiation, Lim3 and MNR2 are expressed by ventral progenitors at a similar developmental stage (FIG. 2J, 2K). To determine the hierarchy of MNR2 and Lim3 activity, we misexpressed Lim3 and assayed the resulting pattern of homeodomain protein expression. Lim3 did not induce MNR2 or Isl2 (FIG. 7A-7E) nor did it increase the number of dorsal Isl1$^+$ neurons (FIG. 7D, 7E). However, there was a very low incidence of ectopic HB9$^+$ neurons in the dorsal spinal cord of Lim3-infected embryos (FIG. 7D, 7E) confined exclusively to cells that coexpressed Isl1 (FIG. 7D; data not shown).

The restriction of ectopic HB9 expression to dorsal Isl1$^+$ neurons in Lim3-infected embryos raised the possibility that the coordinate activities of Lim3 and Isl1 are sufficient to induce HB9 expression. To test this we coinfected embryos with Lim3 and Isl1 viruses (FIG. 7H). The incidence of ectopic expression of HB9 was markedly increased in the spinal cord of such coinfected embryos, compared to embryos infected solely with Lim3 (FIG. 7J, 7K). Moreover, >30% of cells that coexpressed Lim3 and Isl1 expressed HB9 (FIG. 7K) and these HB9$^+$ neurons were not restricted to any dorsoventral position (FIG. 7J; data not shown). In contrast, ectopic expression of Isl2 was rarely detected after Lim3 and Isl1 coinfection (FIG. 7I, 7K; data not shown). These results provide evidence that Lim3 and Isl1 cooperate as intermediaries in the MNR2-induced activation of HB9 expression.

HB9 Activity and the Maintenance of Transcription Factor Expression by Somatic Motor Neurons The expression of MNR2 is transient, raising the issue of how the expression of Lim3, Isl1 and Isl2 is maintained in post-mitotic motor neurons. The HB9 gene encodes a homeodomain protein closely related to MNR2, suggesting that HB9 has an activity similar to that of MNR2. To test this we infected embryos with an HB9 virus and monitored the ectopic expression of Isl1, Isl2 and Lim3. HB9 induced the expression of Isl1, Isl2 and Lim3 at an efficiency similar to that of MNR2 (FIG. 7L-N; data not shown). Misexpression of HB9 also induced the ectopic expression of MNR2 (data not shown), a result that we interpret to reflect mimicry of the autoregulatory activity of MNR2. These results suggest a role for HB9 in maintaining of the differentiated properties of somatic motor neurons at times after MNR2 expression has been extinguished.

Lim3 Expression in the Absence of MNR2 is Sufficient to Induce the V2 Interneuron Fate Lim3 is also expressed by V2 neurons and appears prior to the V2 marker Chx10 (Ericson et al., 1997). We therefore examined whether Lim3 has a role in the differentiation of this interneuron subtype. To test this, we examined the pattern of Chx10 expression in the spinal cord of Lim3-infected embryos. Misexpression of Lim3 induced Chx10 in Cyn1+ neurons located at both dorsal and extreme ventral regions of the spinal cord, adjacent to the floor plate (FIG. 7F, G; data not shown) but not in somatic motor neurons (FIG. 7G). These results suggest that the expression of Lim3 in cells devoid of MNR2 activity is sufficient to direct the differentiation of V2 interneurons.

Discussion

Graded Shh signaling appears to control the identity of neuronal subtypes in the ventral neural tube. The present studies show that Shh induces the expression of a homeodomain protein, MNR2, in motor neuron progenitors and that the expression of MNR2 is sufficient to direct somatic motor neuron differentiation. Thus, MNR2 expression appears to be a critical output of Shh signaling in the pathway of somatic motor neuron generation. We discuss these findings in the context of the Shh signaling pathways involved in neuronal fate determination and the control of progenitor cell identity and commitment in the vertebrate CNS.

MNR2 Expression Specifies Somatic Motor Neuron Progenitors

Shh signaling is required for the generation of somatic motor neurons, but the downstream steps in this developmental program have not been resolved. Somatic motor neurons derive from Pax6+ progenitor cells, yet Pax6 itself appears to be required only indirectly for somatic motor neuron generation (Ericson et al., 1997). Our results suggest that the expression of MNR2 by Pax6+ progenitors is a key step in somatic motor neuron development, specifying ventral cells as motor neuron progenitors.

At what step in the pathway of somatic motor neuron differentiation does MNR2 act? MNR2 is expressed by ventral progenitor cells ~4–5 h prior to the generation of the first post-mitotic motor neurons and the cell cycle time of ventral progenitor cells is ~8 h (Langman et al., 1966). Thus, it appears that MNR2 expression is initiated during the final division cycle of motor neuron progenitors. The onset of MNR2 expression by motor neuron progenitors coincides with the time that they attain independence of Shh signaling (Ericson et al., 1996). This observation and the ability of MNR2 to activate its own expression provide a potential molecular basis for the transition of Shh-dependent ventral progenitor cells into Shh-independent, committed somatic motor neuron progenitors.

MNR2 is induced rapidly by Shh, prior to the expression of other somatic motor neuron transcription factors. It is unclear, however, if MNR2 is a direct target for the conserved Hedgehog (Hh) signal transduction pathway mediated by the Ci/Gli class of transcription factors (Ingham, 1995). Gli proteins have been implicated in floor plate differentiation (Lee et al., 1997; Hynes et al., 1997; Ding et al., 1998; Matise et al., 1998) but it is uncertain whether they are also involved directly in the generation of motor neurons.

MNR2 and the Transcriptional Hierarchy of Motor Neuron Differentiation

The expression of MNR2 in neural progenitor cells appears sufficient to induce somatic motor neurons. Moreover, the ability of MNR2 to direct motor neuron differentiation appears to be independent of the position of progenitor cells within the neural tube. Most strikingly, MNR2 promotes somatic motor neuron differentiation both in ventral progenitors that have been exposed to inadequate levels of Shh and in dorsal progenitor cells that have been exposed to BMP signals (Liem et al., 1997). Since exposure of progenitors to BMPs inhibits motor neuron generation (Basler, et al., 1993), these findings implicate MNR2 as a determinant of somatic motor neuron identity.

MNR2 appears to function upstream of a set of LIM homeodomain transcription factors that cooperate to specify somatic motor neuron identity (FIG. 8). Lim3 is expressed soon after MNR2 in motor neuron progenitors. Ectopic expression of MNR2 induces Lim3 expression but Lim3 does not induce MNR2, suggesting that MNR2 functions upstream of Lim3 in motor neuron progenitors. However, Lim3 is also expressed by V2 neurons that appear to derive from MNR2− progenitors, implying the existence of an MNR2-independent pathway for the activation of Lim3 expression. This parallel pathway could also operate in somatic motor neuron progenitors.

MNR2 efficiently induces the expression of Isl1 in spinal neurons. The induction of Isl1 may be a key step in somatic motor neuron differentiation, since the later appearance of transcription factors specific to somatic motor neurons, Isl2 and HB9, appears to require the expression of Isl1. The role of Isl1 inferred from these gain-of-function studies is consistent with the loss of somatic motor neuron differentiation in mice lacking Isl1 function (Pfaff et al., 1996). Isl1 is also required for the generation of visceral motor neurons (Pfaff et al., 1996). Since MNR2 is not expressed by Nkx2.2+ visceral motor neuron progenitors, the expression of Isl1 in visceral motor neurons appears to be regulated by a factor other than MNR2. A dorsal expansion in the domain of Nkx2.2 expression results in a switch from somatic to visceral motor neuron generation (Ericson et al., 1997) suggesting that Nkx2.2 or related Nkx genes (Pabst et al., 1998) promote visceral motor neuron identity.

Lim3 and Isl1 appear to cooperate in certain of the downstream steps of somatic motor neuron differentiation, their actions being sufficient to induce HB9 but not Isl2. Indeed, biochemical evidence indicates that Isl1 and Lim3 can interact directly (Jurata et al., 1998). Different intermediary pathways may therefore control the expression of distinct components of the somatic motor neuron phenotype (FIG. 8). Although the coexpression of MNR2 and Isl1 can induce Isl2 expression, Lim3 is induced by MNR2 and thus may also participate in the induction of Isl2 expression. HB9 possesses an activity similar to that of MNR2 but appears only in post-mitotic neurons and thus may function to maintain somatic motor neuron properties after the expression of MNR2 has been extinguished.

The expression of Lim3 in a cellular context devoid of MNR2 results in the activation of Chx10, a definitive marker of V2 neurons. Lim3 many therefore function in the normal program of generation of both somatic motor neurons and V2 neurons. Misexpression of MNR2 in the V2 interneuron domain represses the expression of Chx10 while promoting somatic motor neuron differentiation. Thus the restriction in the domain of MNR2 expression imposed by graded Shh signaling may underlie the decision of ventral progenitors to differentiate into somatic motor neurons or V2 neurons.

MNR2 Functions in Conjunction with an Independent Neurogenic Program

The activity of MNR2 in inducing somatic motor neuron differentiation appears to operate within the context of a broader program of neurogenesis. Ectopic MNR2 induces the expression of Lim3 in progenitor cells but induces Isl1, Isl2 and HB9 only in post-mitotic neurons, consistent with the normal temporal appearance of these proteins in somatic motor neurons. Thus, neural progenitors appear unable to express post-mitotic somatic motor neuron markers even though MNR2 is expressed precociously in these cells.

The timing of differentiation of vertebrate neurons appears to be controlled by the sequential activation of basic HLH proteins with neurogenic properties (Anderson and Jan, 1997; Lo et al., 1998). The expression of certain of these bHLH genes is initiated at the time that progenitor cells exit the cell cycle and acquire overt neuronal character (Begley et al., 1992; Roztocil et al., 1997). An independently-regulated program of expression of neurogenic bHLH proteins might therefore limit the ability of MNR2 to induce the expression of Isl1, Isl2 and HB9 to post-mitotic neurons.

A Single Transcription Factor Specifies an Individual Neuronal Subtype

Our results provide some insight into the question of whether neuronal subtype identities in the developing vertebrate CNS are controlled by the actions of dedicated neuronal subtype-specific determinants. Studies of cell fate determination during vertebrate myogenesis and *Drosophila* eye development have revealed the existence of transcriptional cascades that can be activated by the expression of a single transcription factor (Weintraub, 1993; Halder et al., 1995; Chen et al., 1997; Pignoni et al., 1997). Our results indicate that one neuronal subtype generated in the vertebrate CNS, somatic motor neurons, can similarly be specified by the actions of a single homeodomain transcription factor, MNR2. Moreover, in a neuronal context devoid of MNR2 activity, Lim3 appears sufficient to specify V2 interneuron fates. The differentiation of floor plate cells can also be specified by a single transcription factor, the winged helix protein HNF3β (Ruiz i Altaba et al., 1993; 1995; Sasaki and Hogan 1994).

The identification of transcription factors that direct the generation of two distinct classes of neurons in the ventral spinal cord raises the possibility that the identity of neurons in other regions of the CNS are similarly determined by the activity of individual subtype-dedicated transcription factors. The identification of such factors might permit the direction of progenitor cells along specific pathways of neuronal differentiation in the absence of constraints imposed by their prior developmental history.

REFERENCES OF THE EXPERIMENTS

Anderson, D. J. and Jan, Y. N. (1997). The determination of the neuronal phenotype. In Molecular and Cellular Approaches to Neural Development, Eds. Cowan, W. M., Jessell, T. M., and Zipursky, S. L. Oxford University Press, New York, Oxford pp 26–63.

Bang, A. G., and Goulding, M. D. (1996). Regulation of vertebrate neural cell fate by transcription factors. Curr. Opin. Neurobiol. 6, 25–32.

Basler, K., Edlund, T., Jessell, T. M., and Yamada, T. (1993). Control of cell pattern in the neural tube: regulation of cell differentiation by dorsalin-1, a novel TGF beta family member. Cell 73, 687–702.

Begley, C. G., Lipkowitz, S., Gobel, V., Mahon, K. A., Bertness, V., Green, A. R., Gough, N. M., and Kirsch, I. R. (1992). Molecular characterization of NSCL, a gene encoding a helix-loop-helix protein expressed in the developing nervous system. Proc. Natl. Acad. Sci. USA 89, 38–42.

Burke, A. C., and Tabin, C. J. (1996). Virally mediated misexpression of Hoxc-6 in the cervical mesoderm results in spinal nerve truncations. Dev. Biol. 178, 192–197.

Chen, R., Amoui, M., Zhang, Z, and Mardon, G. (1997). Dachshund and eyes absent proteins form a complex and function synergistically to induce ectopic eye development in *Drosophila*. Cell 91, 893–903.

Chiang, C., Litingtung, Y., Lee, E., Young, K. E., Corden, J. L., Westphal, H., and Beachy, P. A. (1996). Cyclopia and defective axial patterning in mice lacking Sonic Hedgehog gene function. Nature 383, 407–413.

Ding, Q, Motoyama, J., Gasca, S., Mo, R., Sasaki, H. Rossant, J., and Hui, C. C. (1998). Diminished sonic hedgehog signaling and lack of floor plate differentiation in Gli2 mutant mice. Development 125, 2533–2543.

Dulac, C., and Axel, R. (1995). A novel family of genes encoding putative pheromone receptors in mammals. Cell 83, 195–206.

Ericson, J., Thor, S., Edlund, T., Jessell, T. M., and Yamada, T. (1992). Early stages of motor neuron differentiation revealed by expression of homeobox gene Islet-1. Science 256, 1555–60.

Ericson, J., Morton, S., Kawakami, A., Roelink, H., and Jessell, T. M. (1996). Two critical periods of sonic hedgehog signaling required for the specification of motor neuron identity. Cell 87, 661–673.

Ericson, J., Rashbass, P., Schedl, A., Brenner-Morton, S., Kawakami, A., van Heyningen, V., Jessell, T. M., and Briscoe, J. (1997). Pax6 controls progenitor cell identity and neuronal fate in response to graded Shh signaling. Cell 90, 169–180.

Fedtsova, N., and Turner, E. E. (1997). Inhibitory effects of ventral signals on the development of Brn-3.0-expressing neurons in the dorsal spinal cord. Dev. Biol. 190, 18–31.

Halder, G., Callaerts, P. and Gehring, W. J. (1995). Induction of ectopic eyes by targeted expression of the eyeless gene in *Drosophila*. Science 267, 1788–1792.

Hamburger, H., and Hamilton, H. (1951). A series of normal stages in the development of the chick embryo. J. Morphol. 88, 49–92.

Harrison, K. A., Druey, K. M., Deguchi, Y., Tuscano, J. M., and Kehrl, J. H. (1994). A novel human homeobox gene distantly related to proboscipedia is expressed in lymphoid and pancreatic tissues. 269, 19968–19975.

Hynes, M., Stone, D. M., Dowd M., Pitts-Meek, S., Goddard, A., Gurney, A., and Rosenthal, A. (1997). Control of cell pattern in the neural tube by the zinc finger transcription factor and oncogene Gli-1. Neuron 19, 15–26.

Hughes, S. H., Greenhouse, J. J., Petropoulos C. J., and Sutrave, P. (1987). Adaptor plasmids simplify the insertion of foreign DNA into helper-independent retroviral vectors. J. Virol. 61, 3004–3012.

Ingham, P. W. (1995). Signaling by hedgehog family proteins in *Drosophila* and vertebrate development. Curr. Opin. Genet Dev. 5, 492–498.

Jurata, L. W., Pfaff, S. L., Gill G. N. (1998). The nuclear LIM domain interactor NLI mediates homo-and heterodimerization of Lim domain transcription factors. J. Biol. Chem. 273, 3152–3157.

Langman, J., Guerrant, R. L., and Freeman, B. G. (1966). Behavior of neuroepithelial cells during closure of the neural tube. J. Comp. Neurol. 127, 399–411.

Leber, S. M., and Sanes, J. R. (1995). Migratory paths of neurons and glia in the embryonic chick spinal cord. J. Neurosci. 15, 1236–1248.

Lee, J., Platt, K. A., Censullo, P., and Ruiz i Altaba, A. (1997). Gli1 is a target of Sonic hedgehog that induces ventral neural tube development. Development 124, 2537–2552.

Liem, K. F. Jr, Tremml, G., and Jessell, T. M. (1997). A role for the roof plate and its resident TGFbeta-related proteins in neuronal patterning in the dorsal spinal cord. Cell 91, 127–138.

Lo L, Tiveron M. C., and Anderson D. J. (1998). MASH1 activates expression of the paired homeodomain transcription factor Phox2a, and couples pan-neuronal and subtype-specific components of autonomic neuronal identity. Development 125 609–620.

Lumsden, A., and Krumlauf, R. (1996). Patterning the vertebrate neuraxis. Science 274, 1109–1115.

Marti, E., Bumcrot, D. A., Takada, R., and McMahon, A. P. (1995). Requirement of 19K form of sonic hedgehog for induction of distinct ventral cell types. Nature 375, 322–325.

Matise M. P., Epstein D. J., Park H. L., Platt K. A. and Joyner A. L. (1998). Gli2 is required for induction of floor plate and adjacent cells, but not most ventral neurons in the mouse central nervous system. Development 125 2759–2770.

Morgan, B. A. and Fekete, D. M. (1996). Manipulating gene expression with replication-competent retroviruses. Methods Cell Biol. 51, 185–218.

Osumi, N., Hirota, A., Ohuchi, H., Nakafuku, M., Iimura, T., Kuratani, S., Fujiwara, M., Noji, S., and Eto, K. (1997). Pax-6 is involved in specification of the hindbrain motor neuron subtype. Development 124, 2961–2972.

Pabst, O., Herbrand, H., and Arnold, H. H. (1998). Nkx2-9 is a novel homeobox transcription factor which demarcates ventral domains in the developing mouse CNS. Mech. Dev. 73, 85–93.

Pattyn, A., Morin, X., Cremer, H., Goridis, C., and Brunet, J. F. (1997). Expression and interactions of the two closely related homeobox genes Phox2a and Phox2b during neurogenesis. Development 124, 4065–4075.

Pfaff, S. L., Mendelsohn, M., Stewart, C. L., Edlund, T., and Jessell, T. M. (1996). Requirement for LIM homeobox gene Isl1 in motor neuron generation reveals a motor neuron-dependent step in interneuron differentiation. Cell 84, 309–320.

Pfaff, S., and Kintner, C. (1998). Neuronal diversification: development of motor neuron subtypes. Curr. Opin. Neurobiol. 8, 27–36.

Pignoni, F., Hu, B., Zavitz, K. H., Xiao, J., Garrity, P. A., and Zipursky, S. L. (1997). The eye-specification proteins So and Eya form a complex and regulate multiple steps in *Drosophila* eye development. Cell 91, 881–891.

Riddle, R. D., Ensini, M., Nelson, C., Tsuchida, T., Jessell, T. M., and Tabin, C. (1995). Induction of the LIM homeobox gene Lmx1 by WNT7 a establishes dorsoventral pattern in the vertebrate limb. Cell 83, 631–640.

Roelink, H., Porter, J. A., Chiang, C., Tanabe, Y., Chang, D. T., Beachy, P. A., and Jessell, T. M. (1995). Floor plate and motor neuron induction by different concentrations of the amino-terminal cleavage product of sonic hedgehog autoproteolysis. Cell 81, 445–455.

Roztocil, T., Matter-Sadzinski, L., Alliod, C., Ballivet, M., and Matter, J. M. (1997). NeuroM, a neural helix-loop-helix transcription factor, defines a new transition stage in neurogenesis. Development 124, 3263–3272.

Ruiz i Altaba, A., Cox, C., Jessell, T. M., and Klar, A. (1993). Ectopic neural expression of a floor plate marker in frog embryos injected with the midline transcription factor Pintallavis. Proc. Natl. Acad. Sci. USA 90, 8268–8272.

Ruiz i Altaba, A., Jessell, T. M., and Roelink, H. (1995). Restrictions to floor plate induction by hedgehog and winged-helix genes in the neural tube of frog embryos. Mol. Cell Neurosci. 6, 106–121.

Saha, M. S., Miles, R. R., and Grainger, R. M. (1997). Dorsal-ventral patterning during neural induction in *Xenopus:* assessment of spinal cord regionalization with xHB9, a marker for the motor neuron region. Dev. Biol. 187, 209–223.

Sasaki, H., and Hogan, B. L. (1994). HNF-3 beta as a regulator of floor plate development. Cell 76, 103–115.

Schaeren-Wiemers, N. and Gerfin-Moser, A. (1993). A single protocol to detect transcripts of various types and expression levels in neural tissue and cultured cells: in situ hybridization using digoxigenin-labelled cRNA probes. Histochemistry 100, 431–440.

Tanabe, Y., Roelink, H., and Jessell, T. M. (1995). Induction of motor neurons by sonic hedgehog is independent of floor plate differentiation. Curr. Biol. 5, 651–658.

Tanabe, Y., and Jessell, T. M. (1996). Diversity and pattern in the developing spinal cord. Science 274, 1115–1123.

Tanaka, H., and Obata, K. (1984). Developmental changes in unique cell surface antigens of chick embryo spinal motor neurons and ganglion cells. Dev. Biol. 106, 26–37.

Tsuchida, T., Ensini, M., Morton, S. B., Baldassare, M., Edlund, T., Jessell, T. M., and Pfaff, S. L. (1994). Topographic organization of embryonic motor neurons defined by expression of LIM homeobox genes. Cell 79, 957–70.

Varela-Echavarría, A., Pfaff, S. L., and Guthrie, S. (1996). Differential Expression of LIM homeobox genes among motor neuron subpopulations in the developing chick brain stem. Mol. Cell. Neurosci. 8, 242–257.

Weintraub, H. (1993). The MyoD family and myogenesis: redundancy, networks, and thresholds. Cell 75, 1241–1244.

Westendorf, J. M., Rao, P. N., and Gerace, L. (1994). Cloning of cDNAs for M-phase phosphoproteins recognized by the MPM2 monoclonal antibody and determination of the phosphorylated epitope. Proc. Natl. Acad. Sci. USA 91, 714–718.

Yamada, T., Pfaff, S. L., Edlund, T., and Jessell, T. M. (1993). Control of cell pattern in the neural tube: motor neuron induction of diffusible factors from notochord and floor plate. Cell 73, 673–86.

What is claimed is:

1. A method of inducing a chick neural progenitor cell to differentiate into a chicken somatic motor neuron which comprises expressing in a chick spinal cord motor neuron progenitor cell a protein comprising consecutive amino acids having the amino acid sequence set forth in SEQ ID NO:1 which encodes a homeobox motor neuron restricted pattern protein designated MNR2, so as to thereby induce the chick spinal cord motor neuron progenitor cell to differentiate into a chicken somatic motor neuron.

2. The method of claim 1, wherein the expression of the protein induces expression of transcription factors Isl2, Lim 3 and HB9.

3. A method of inducing a chick hindbrain motor neuron progenitor cell to differentiate into a chicken somatic motor neuron which comprises expressing in a chick hindbrain motor neuron progenitor cell a protein comprising consecutive amino acids having the amino acid sequence set forth in SEQ ID NO:1 which encodes a homeobox motor neuron restricted pattern protein designated MNR2, so as to thereby induce the chick neural progenitor cell to differentiate into a chicken somatic motor neuron.

4. The method of claim 3, wherein the expression of the protein induces expression of transcription factors Isl2, Lim 3 and HB9.

* * * * *

SEQUENCE LISTING

<160> NUMBER OF SEQ ID NOS: 5

<210> SEQ ID NO 1
<211> LENGTH: 300

<212> TYPE: PRT
<213> ORGANISM: CHICK EMBRYO

<400> SEQUENCE: 1

```
Met His Lys Pro Met Glu Lys Ser Gln Asn Phe Arg Ile Glu Ala Leu
 1               5                  10                  15
Leu Ala Glu Lys Pro Pro Arg Ser Ala Ser Pro Pro Gly Leu Ser Pro
                20                  25                  30
Ala Gly Ser Pro Gly Pro Ala Gly Arg Thr Asp Thr Pro Ser Pro Arg
            35                  40                  45
Ala Pro Gln Ala Ala Thr Pro Leu Gly Pro Ala Gly Phe Val Pro Lys
50                  55                  60
Pro Gly Leu Leu His Leu Pro Gly Pro Gly Leu Gly Thr Leu Pro Ala
65                  70                  75                  80
Leu Tyr Pro Pro Ala Val Tyr Pro Leu Pro Ala Leu Gly Gly Gln His
                85                  90                  95
Ala Ala Phe Ala Tyr Thr Ala Phe Pro Gln Leu Pro Pro Pro Gly Ala
            100                 105                 110
Glu His Leu Lys Ala Ala Val Ala Gly Ser Phe Pro Leu Glu Gln Trp
        115                 120                 125
Ile Arg Ala Gly Met Leu Val Pro Arg Leu Ser Asp Phe His Ala Thr
130                 135                 140
Pro Gln Ser Ala Leu Met Gly Lys Ser Arg Arg Pro Arg Thr Ala Phe
145                 150                 155                 160
Thr Ser Gln Gln Leu Leu Glu Leu Glu Asn Gln Phe Lys Leu Asn Lys
                165                 170                 175
Tyr Leu Ser Arg Pro Lys Arg Phe Glu Val Ala Thr Ser Leu Met Leu
            180                 185                 190
Thr Glu Thr Gln Val Lys Ile Trp Phe Gln Asn Arg Arg Met Lys Trp
        195                 200                 205
Lys Arg Ser Arg Lys Ala Lys Glu Gln Gly Met Ala Val Glu Pro Glu
210                 215                 220
Lys Pro Arg Gly Leu Gly Lys Ala Asp Glu Ser Leu Leu Pro Ser Gln
225                 230                 235                 240
Pro Gln Gly Gln Ala Gly Asp Ser Pro Glu Phe Val Gly Cys Ser Pro
                245                 250                 255
Gly Thr Gly Phe Leu Cys Arg Ser Ala Glu Leu Gly Tyr Asp Pro Asp
            260                 265                 270
Ser Ser Cys Ser Gly Gly Glu Glu Asp Glu Glu Glu Asp Asp Gly
        275                 280                 285
Met Asp Thr Ala Glu Arg Lys Met Gly Ser Val Leu
290                 295                 300
```

<210> SEQ ID NO 2
<211> LENGTH: 1736
<212> TYPE: DNA
<213> ORGANISM: CHICK EMBRYO

<400> SEQUENCE: 2

```
cagatctgct cccagatgct ctgcctctcc tcgaaggcca gagtcggtgg gtccgggcca    60
gctctgctcc tgctcacccg cctgtcccag agcagccaag gctttcatct ccacctgttt   120
ctggtgcctt cacctggaga agaccaaacc gagcaaataa ataacaatct gcccgtatgc   180
acctgctcca tgggcttctt gggcggatag acgatgcagg gttgtggccc ctgcgtgcag   240
ccagctcggg cccgctgatg tccccgtgcc aaagaggtgc aaagaggaac ggcacggggt   300
```

-continued

```
gtgaagagca ggatcgggcc ccggggtgtg ccgaggggct gcggaagccg ggggagggag    360
gccgggccga cggggcgggg ggccggcggg gagccaatag ggagctgggg caggtggagg    420
gggggggttaa aaccccccg gtggcggcgg gcaagcgagt gccgggagg aggagcggtg     480
aggagggctg cccctgaggg cagcggaggc cggcgcggcc ccgcgagtga atgcccgccg    540
gtgccgggt ggcccggggc tgcccggccg ggcgctgccc tggcagccga gcggcggggg     600
gaggcacgct gcgttttcgc ggggcccggc cgggccatgc acaaacccat ggagaagtcc    660
caaaacttcc gcatcgaggc gctcctggct gagaagccgc cgcggagcgc ctctcctccg    720
gggctcagcc ccgcgggcag ccccggcccc gccggccgta ccgacacccc ctcgcctcgg    780
gctccccagg ccgccacccc cctcggcccg gcgggcttcg tccccaaacc cggcttgctg    840
cacctccccg gccccgggct gggcaccctg ccggccctct accgcctgc cgtgtacccg     900
ctgccggcct ggggggccca gcacgccgct ttcgcctaca ccgccttccc ccagctgccg    960
ccgcccggcg ccgagcacct gaaggcggcg gtggccggtt ccttcccgct ggagcagtgg   1020
atccgagccg ggatgctcgt gccgaggctc tccgacttcc acgccacccc acagtccgcc   1080
ttgatgggaa agtcgcgccg gccccgcacc gccttcacca gccagcagct gctggagctg   1140
gagaaccagt tcaagctcaa caagtatctg tccaggccca agcgcttcga ggtggccacg   1200
tcgctgatgc tcactgagac gcaggtgaag atctggttcc agaaccgccg catgaagtgg   1260
aagcggagcc gcaaagccaa ggagcagggg atggcagtgg agcccgagaa gccacggggg   1320
cttggcaaag ctgatgagag tctgctgccc agccagcccc agggacaggc tggtgacagc   1380
cccgagtttg tggggtgcag ccccggaacg ggcttcctgt gccgcagcgc cgagctgggc   1440
tatgacccgg actcctcctg ttcaggggga gaggaggatg aggaagagga ggacgatggg   1500
atggacactg cggagaggaa gatgggctct gtgttgtgaa gaggttcccg ggtgaggagt   1560
tggaccagtc tcggctggca gacacagact gtgcccatgt gcagcgtggg ggctgagggg   1620
agcctgcccc cccctccctt taacttatgt gtgtttggag tctatttaat gtgtaattat   1680
tcctgtgtgt atcttggggt ttccccacat ccctccccta taaagctgtt atccgg       1736
```

<210> SEQ ID NO 3
<211> LENGTH: 349
<212> TYPE: PRT
<213> ORGANISM: CHICK EMBRYO

<400> SEQUENCE: 3

```
Met Glu Lys Ser Lys Asn Phe Arg Ile Asp Ala Leu Leu Ala Val Asp
1               5                   10                  15

Pro Pro Lys Ala Ala Ala Gln Ser Ala Pro Leu Ala Leu Val Thr Gly
            20                  25                  30

Gly Ser Gly Gly Gly Ser Pro Pro Ser Ser Ser Ser Ser Ser Ser Ser
        35                  40                  45

Ser Ser Ser Ser Ser Ser Glu Leu Pro Ala Asp Cys Pro Arg Thr Asp
    50                  55                  60

Ser Pro Ser Pro Pro Arg Leu Leu Pro Ala His Cys Ala Leu Leu Pro
65                  70                  75                  80

Lys Ala Ala Phe Leu Gly Gly Gly Gly Pro Gly Gly His Pro Gln
            85                  90                  95

His His Ala Leu Gly Leu His Pro Ala Gly Pro Gly Gly Pro Gly Leu
            100                 105                 110

Tyr Gly His Pro Val Tyr Gly Tyr Pro Ala Leu Gly Gly Gln His Pro
```

```
                115                 120                 125
Ala Leu Ser Tyr Ser Tyr Ser Gln Val Gln Gly Ala His Pro Ala His
        130                 135                 140

Pro Ser Ala Asp Pro Ile Lys Leu Ser Ala Gly Thr Phe Gln Leu Asp
145                 150                 155                 160

Gln Trp Leu Arg Ala Ser Thr Ala Gly Met Ile Leu Pro Lys Met Pro
                165                 170                 175

Asp Phe Gly Ser Gln Ala Gln Ser Asn Leu Leu Gly Lys Cys Arg Arg
            180                 185                 190

Pro Arg Thr Ala Phe Thr Ser Gln Gln Leu Leu Glu Leu Glu His Gln
        195                 200                 205

Phe Lys Leu Asn Lys Tyr Leu Ser Arg Pro Lys Arg Phe Glu Val Ala
    210                 215                 220

Thr Ser Leu Met Leu Thr Glu Thr Gln Val Lys Ile Trp Phe Gln Asn
225                 230                 235                 240

Arg Arg Met Lys Trp Lys Arg Gln Lys Lys Ala Lys Glu Gln Ala Ala
                245                 250                 255

Gln Glu Ala Glu Asn Glu Lys Gly Gly Gly Gly Glu Asp Lys Ser
            260                 265                 270

Gly Pro Arg Glu Leu Leu Pro Gly Pro Glu Lys Gly Gly Gly Arg
        275                 280                 285

Arg Leu Arg Glu Leu Pro Asp Ser Glu Pro Glu Asp Glu Glu Glu
    290                 295                 300

Glu Glu Glu Glu Glu Ala Glu Ala Gly Arg Cys Cys Pro Tyr His
305                 310                 315                 320

Ser Ser Asp Cys Ser Glu Ala Asp Glu Glu Asp Ser Gln Ser Gly Gly
                325                 330                 335

Arg Pro Gly Ala Pro Pro Pro Pro Ala Gln Pro Gln
        340                 345

<210> SEQ ID NO 4
<211> LENGTH: 1514
<212> TYPE: DNA
<213> ORGANISM: CHICK EMBRYO

<400> SEQUENCE: 4
ccgggctggc ctctcgccgc ctccgccgct cccatggaaa atccaaaaaa tttccgcatc      60
gacgcgctgc tggctgtcga tccccccaag gcggcggcgc agagcgctcc gctggccctg     120
gtcaccggcg gctccggcgg cggcagccct ccgtcttcgt cgtcctcctc gtcgtcgtcg     180
tcctcctctt cttccgagct ccccgccgac tgcccgcgca ccgacagccc ctctccgcct     240
cgcctgctgc ccgcgcactg cgcgctgctg cccaaagccg ccttcctggg cggggggga      300 ccgggggcg gccacccgca gcaccacgcc ctggggctgc accccgcggg gccgggcggg     360
ccgggcctct acgggcaccc ggtgtacggc tacccgcgt gggcgggca gcacccggcg     420 ctctcctatt cctattcgca agtgcaggga gcgcaccccg cgcatccctc gccgaccccc     480
atcaagctga gcgccggcac ctttcagctg accagtggc tgcgggcgag cacggccggc     540
atgatcctgc ccaaaatgcc cgacttcggc tctcaggcgc agtccaacct gctggggaag     600
tgccggcggc cgcgcaccgc cttcaccagc agcagctgc tggagctgga gcaccagttc     660
aaactcaaca gtacctctcc ccggcccaag cgcttcgagg tggccacgtc gctgatgctc     720
accgagacgc aggtgaagat ttggttccag aaccgccgca tgaaatggaa gcgccagaaa     780
aaggcgaagg agcaggcggc gcaggaggca gagaacgaga aggaggagg aggaggagag     840
```

```
gacaaaagcg ggccgaggga actgctgctg cccggcccgg agaaaggcgg cgggaggcgg      900
ctgagggagc tgcccgacag cgagcccgag gacgaggagg aggaagaaga ggaggaagag      960
gaggccgagg ccgggcggtg ctgcccctac cactcctccg actgctccga ggcggacgag     1020
gaggactcgc agtccggagg acggcccgga gccccccgc caccccccgc acagccgcag     1080
tgagcccacg gccgccccgt cggggccgcc cccggcaacg gagcctcctg gccccgctct     1140
ccatcccgct ctcccatccc tccctgctcg gaggggacg cggaaaggga tctcccgtct      1200
gccgagcggg agggaggatt cacacagtgt tattattgac tgagaagcgg ccacgacttg     1260 agccccctc cccgccccgc cctatcggaa ccgtttcctt cttaccatat atcgggaaaa     1320
gtgtttatgt catgaacgtt aaaactgctg cagatctcaa tactgtcttt attttgtata     1380
tcctatttat aaaaaaggca aaatgaattc ctctacttat gcatgctaaa ttattaccca     1440
gccccttccg cctgaggtgg ggggaggaa tataaataaa gagcgttttg tactgtgaaa     1500
aaaaaaaaaa aaaa                                                      1514

<210> SEQ ID NO 5
<211> LENGTH: 14
<212> TYPE: PRT
<213> ORGANISM: CHICK EMBRYO

<400> SEQUENCE: 5

Met Glu Lys Ser Lys Asn Phe Arg Ile Asp Ala Leu Leu Ala
1               5                   10
```